(12) United States Patent
Glimcher et al.

(10) Patent No.: US 6,573,365 B1
(45) Date of Patent: Jun. 3, 2003

(54) ANTIBODIES FOR NF-AT INTERACTING PROTEIN, NIP45

(75) Inventors: Laurie H. Glimcher, West Newton, MA (US); Martin R. Hodge, Arlington, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 09/617,923

(22) Filed: Jul. 17, 2000

Related U.S. Application Data

(62) Division of application No. 09/192,611, filed on Nov. 16, 1998, now Pat. No. 6,090,561, which is a division of application No. 08/755,584, filed on Nov. 25, 1996, now Pat. No. 5,858,711.

(51) Int. Cl.$^7$ ............................................. C07K 16/24
(52) U.S. Cl. ............................. 530/388.22; 530/387.1; 530/387.9; 530/388.1; 530/388.2; 530/391.1; 530/391.3
(58) Field of Search .......................... 424/130.1, 139.1, 424/152.1; 590/387.1, 388.2; 530/391.1

(56) References Cited

PUBLICATIONS

Skolnick et al. Trends in Biotech. 18: 34–39 (2000).*
Ngo et al. in The Protein Folding Problem and Tertiary Structure Prediction, 1994, Merz et al. (Ed.), Birkhauser, Boston, MA pp 433, 492–495.*
Lederman et al. Molecular Immunology 28: 1171–1181 (1991).*
Li et al. PNAS 77: 3211–3214 (1980).*
Peltz Current Opinion in Biotechnology 8: 467–473 (1997).*
Manning et al. in Inflammation: Basic Principles and Clinical Correlates, 3rd Ed., Gallin and Snyderman (Eds.) Lippincott Williams & Wilkins, Philadelphia 1999, pp. 1159–1176.*
Hillier et al., EST Database Accession No. AA063239 (dated Dec. 23, 1997).
Hillier et al., EST Database Accession No. AA063239 (dated Sep. 24, 1996).
Sasaki et al. EST Database Accession No. D49049 (dated Aug. 2, 1995).
Minobe et al. EST Database Accession No. D24170 (dated Dec. 7, 1994).
Minobe et al. EST Database Accession No. D24480 (dated Jan. 14, 1994).
Sasaki, EST Database Accession No. C20299 (dated Oct. 24, 1996).
Fujiwara et al., EST Database Accession No. C18242 (datd Oct. 2, 1996).
Xie, Genbank Database Accession No. HSU40215 (dated Oct. 5, 1996).
Casolaro, V., et al., "Inhibition of NF–AT–dependent transcription by NF –kappa B: implications for differential gene expression in T helper cell subsets", *Proc Natl Acad Sci USA*, vol. 92, pp. 11623–11627 (1995).
Ho, I–C. et al., "The Proto–Oncogene c–maf is Responsible for Tissue–Specific Expression of Interleukin–4", Cell, vol. 85, pp. 973–983 (1996).
Hodge, M.R. et al., "The proximal promoter of the IL–4 gene is composed of multiple essential regulatory sites that bind at least two distinct factors", *Journal of Immunology* vol. 154, No. 12, pp. 6397–6405 (1995).
Hodge, M.R. et al., "Hyperproliferation and dysregulation of IL–4 expression in NF–ATp–deficient mice", *Immunity* vol. 4, pp. 397–405 (1996).
Rooney, J.W. et al., "A common factor regulates both Th10 and Th2 –specific cytokine gene expression", *EMBO Journal*, vol. 13(3), pp. 625–633 (1994).
Rooney, J.W. et al., "Coordinate and cooperative roles for NF –AT and AP–1 in the regulation of the murine IL—4 gene", *Immunity*, vol. 2, pp. 473–483 (1995).
Tara, D. et al., "Characterization of the constitutive and inducible components of a T cell IL –4 activation responsive element", *J Immunol*, vol. 154(9), pp. 4592–4602 (1995).

* cited by examiner

*Primary Examiner*—Phillip Gambel
(74) *Attorney, Agent, or Firm*—Lahive & Cockfield, LLP; Megan E. Williams, Esq.

(57) ABSTRACT

Isolated nucleic acid molecules encoding a novel protein, NIP45, that interacts with members of the Nuclear Factor of Activated T cell (NF-AT) family of proteins, are disclosed. The invention further provides antisense nucleic acid molecules, recombinant expression vectors containing a nucleic acid molecule of the invention, host cells into which the expression vectors have been introduced and non-human transgenic animals carrying a NIP45 transgene. The invention further provides isolated NIP45 proteins and peptides, NIP45 fusion proteins and anti-NIP45 antibodies. Methods of using the NIP45 compositions of the invention are also disclosed, including methods for detecting NIP45 protein or mRNA in a biological sample, methods of modulating NIP45 activity in a cell, and methods for identifying agents that modulate an interaction between NIP45 and an NF-AT family protein.

3 Claims, 14 Drawing Sheets

NFATp

Max

CDK2 pEG202

| | |
|---|---|
| ACAGTGTGGGAGATGGCGGAACCACTGAGGGGACGTGGTCCGAGGTCC | 48 |
| TGTCACACCCTCTACCGCCTTGGTGACTCCCCTGCACCAGGCTCCAGG | |
|         M   A   E   P   L   R   G   R   G   P   R   S | 12 |
| | |
| CGCGGTGGCCGAGGCGCTCGGAGAGCCCGAGGCGCCCGTGGCCGGTGT | 96 |
| GCGCCACCGGCTCCGCGAGCCTCTCGGGCTCCGCGGGCACCGGCCACA | |
|  R   G   G   R   G   A   R   R   A   R   G   A   R   G   R   C | 28 |
| | |
| CCTCGCGCCCGGCAGTCTCCGGCTAGGCTCATTCCAGACACCGTGCTT | 144 |
| GGAGCGCGGGCCGTCAGAGGCCGATCCGAGTAAGGTCTGTGGCACGAA | |
|   P   R   A   R   Q   S   P   A   R   L   I   P   D   T   V   L | 44 |
| | |
| GTGGACTTGGTCAGTGACAGCGACGAAGAGGTCTTGGAAGTCGCAGAC | 192 |
| CACCTGAACCAGTCACTGTCGCTGCTTCTCCAGAACCTTCAGCGTCTG | |
|    V   D   L   V   S   D   S   D   E   E   V   L   E   V   A   D | 60 |
| | |
| CCAGTAGAGGTGCCGGTCGCCCGCCTCCCCGCGCCGGCTAAACCTGAG | 240 |
| GGTCATCTCCACGGCCAGCGGGCGGAGGGGCGCGGCCGATTTGGACTC | |
|    P   V   E   V   P   V   A   R   L   P   A   P   A   K   P   E | 76 |
| | |
| CAGGACAGCGACAGTCACAGTGAAGGGGCGGCCGAGGGGCCTGCGGGA | 288 |
| GTCCTGTCGCTGTCACTGTCACTTCCCCGCCGGCTCCCCGGACGCCCT | |
|    Q   D   S   D   S   D   S   E   G   A   A   E   G   P   A   G | 92 |
| | |
| GCCCCGCGTACATTGGTGCGACGGCGGCGGCGGCGGCTGCTGGATCCC | 336 |
| CGGGGCGCATGTAACCACGCTGCCGCCGCCGCCGACGACCTAGGG | |
|    A   P   R   T   L   V   R   R   R   R   R   L   L   D   P | 108 |
| | |
| GGAGAGGCGCCGGTGGTCCCAGTGTACTCCGGGAAGGTACAGAGCAGC | 384 |
| CCTCTCCGCGGCCACCAGGGTCACATGAGGCCCTTCCATGTCTCGTCG | |
|    G   E   A   P   V   V   P   V   Y   S   G   K   V   Q   S   S | 124 |
| | |
| CTCAACCTCATTCCAGATAATTCATCCCTCTTGAAACTGTGCCCTTCA | 432 |
| GAGTTGGAGTAAGGTCTATTAAGTAGGGAGAACTTTGACACGGGAAGT | |
|    L   N   L   I   P   D   N   S   S   L   L   K   L   C   P   S | 140 |
| | |
| GAGCCTGAAGATGAGGCAGATCTGACAAATTCTGGCAGTTCTCCCTCT | 480 |
| CTCGGACTTCTACTCCGTCTAGACTGTTTAAGACCGTCAAGAGGGAGA | |
|    E   P   E   D   E   A   D   L   T   N   S   G   S   S   P   S | 156 |
| | |
| GAGGATGATGCCCTGCCTTCAGGTTCTCCCTGGAGAAAGAAGCTCAGA | 528 |
| CTCCTACTACGGGACGGAAGTCCAAGAGGGACCTCTTTCTTCGAGTCT | |
|    E   D   D   A   L   P   S   G   S   P   W   R   K   K   L   R | 172 |

FIGURE 4A

```
AAGAAGTGTGAGAAAGAAGAAAAGAAAATGGAAGAGTTTCCGGACCAG                576
TTCTTCACACTCTTTCTTCTTTTCTTTTACCTTCTCAAAGGCCTGGTC
  K   K   C   E   K   E   E   K   K   M   E   E   F   P   D   Q    188

GACATCTCTCCTTTGCCCCAACCTTCGTCAAGGAACAAAAGCAGAAAG                624
CTGTAGAGAGGAAACGGGGTTGGAAGCAGTTCCTTGTTTTCGTCTTTC
  D   I   S   P   L   P   Q   P   S   S   R   N   K   S   R   K    204

CATACGGAGGCGCTCCAGAAGCTAAGGGAAGTGAACAAGCGTCTCCAA                672
GTATGCCTCCGCGAGGTCTTCGATTCCCTTCACTTGTTCGCAGAGGTT
    H   T   E   A   L   Q   K   L   R   E   V   N   K   R   L   Q  220

GATCTCCGCTCCTGCCTGAGCCCCAAGCAGCACCAGAGTCCAGCCCTT                720
CTAGAGGCGAGGACGGACTCGGGGTTCGTCGTGGTCTCAGGTCGGGAA
    D   L   R   S   C   L   S   P   K   Q   H   Q   S   P   A   L  236

CAGAGCACAGATGATGAGGTGGTCCTAGTGGAAGGGCCTGTCTTGCCA                768
GTCTCGTGTCTACTACTCCACCAGGATCACCTTCCCGGACAGAACGGT
    Q   S   T   D   D   E   V   V   L   V   E   G   P   V   L   P  252

CAGAGCTCTCGACTCTTTACACTCAAGATCCGGTGCCGGGCTGACCTA                816
GTCTCGAGAGCTGAGAAATGTGAGTTCTAGGCCACGGCCCGACTGGAT
    Q   S   S   R   L   F   T   L   K   I   R   C   R   A   D   L  268

GTGAGACTGCCTGTCAGGATGTCGGAGCCCCTTCAGAATGTGGTGGAT                864
CACTCTGACGGACAGTCCTACAGCCTCGGGGAAGTCTTACACCACCTA
    V   R   L   P   V   R   M   S   E   P   L   Q   N   V   V   D  284

CACATGGCCAATCATCTTGGGGTGTCTCCAAACAGGATTCTTTTGCTT                912
GTGTACCGGTTAGTAGAACCCCACAGAGGTTTGTCCTAAGAAAACGAA
    H   M   A   N   H   L   G   V   S   P   N   R   I   L   L   L  300

TTTGGAGAGAGTGAACTGTCTCCTACTGCCACCCCTAGTACCCTAAAG                960
AAACCTCTCTCACTTGACAGAGGATGACGGTGGGGATCATGGGATTTC
    F   G   E   S   E   L   S   P   T   A   T   P   S   T   L   K  316

CTTGGAGTGGCTGACATCATTGATTGTGTGGTGCTAGCAAGCTCTTCA              1008
GAACCTCACCGACTGTAGTAACTAACACACCACGATCGTTCGAGAAGT
    L   G   V   A   D   I   I   D   C   V   V   L   A   S   S   S  332

GAGGCCACAGAGACATCCCAGGAGCTCCGGCTCCGGGTGCAGGGGAAG              1056
CTCCGGTGTCTCTGTAGGGTCCTCGAGGCCGAGGCCCACGTCCCCTTC
    E   A   T   E   T   S   Q   E   L   R   L   R   V   Q   G   K  348
```

FIGURE 4B

```
GAGAAACACCAGATGTTGGAGATCTCACTGTCTCCTGATTCTCCTCTT                1104
CTCTTTGTGGTCTACAACCTCTAGAGTGACAGAGGACTAAGAGGAGAA
  E   K   H   Q   M   L   E   I   S   L   S   P   D   S   P   L  364

AAGGTTCTCATGTCACACTATGAGGAAGCCATGGGACTCTCTGGACAC                1152
TTCCAAGAGTACAGTGTGATACTCCTTCGGTACCCTGAGAGACCTGTG
  K   V   L   M   S   H   Y   E   E   A   M   G   L   S   G   H  380

AAGCTCTCCTTCTTCTTTGATGGGACAAAGCTTTCAGGCAAGGAGCTG                1200
TTCGAGAGGAAGAAGAAACTACCCTGTTTCGAAAGTCCGTTCCTCGAC
  K   L   S   F   F   F   D   G   T   K   L   S   G   K   E   L  396

CCAGCTGATCTGGGCCTGGAATCCGGAGATCTCATCGAAGTCTGGGGC                1248
GGTCGACTAGACCCGGACCTTAGGCCTCTAGAGTAGCTTCAGACCCCG
  P   A   D   L   G   L   E   S   G   D   L   I   E   V   W   G  412

TGAAGCTCTCACCCTGTTCGGACGCAAAGCCAAGACATGGAGACAATA                1296
ACTTCGAGAGTGGGACAAGCCTGCGTTTCGGTTCTGTACCTCTGTTAT

GCTCCCAATTTTATTATTGTGATTTTTCGCCCCATAAGGGCTAACAGA                1344
CGAGGGTTAAAATAATAACACTAAAAAGCGGGGTATTCCCGATTGTCT

AACTGAATTAGAACTTGTTTACTTATTTATTTCTGGTGCTGGGGATTG                1392
TTGACTTAATCTTGAACAAATGAATAAATAAAGACCACGACCCCTAAC

AACCCCAGACTATGCACATGCTAAGGATGTATGAAGTGGAGGCAAAAC                1440
TTGGGGTCTGATACGTGTACGATTCCTACATACTTCACCTCCGTTTTG

CAAGGCATTACCTTTAGCCAGCCTCTAGTAGACTGTAGTGTCAAGCAA                1488
GTTCCGTAATGGAAATCGGTCGGAGATCATCTGACATCACAGTTCGTT

GTGGCTACTTGGTAGTTGTGTGGCTCTGTGTATGTTTGTGCTGTATTT                1536
CACCGATGAACCATCAACACACCGAGACACATACAAACACGACATAAA

GGCAGCCCCTGGGGCACATAGAAGGGACCTTGGCTTCCCTACCATTTC                1584
CCGTCGGGGACCCCGTGTATCTTCCCTGGAACCGAAGGGATGGTAAAG
```

FIGURE 4C

```
ACGTTCGCTGGTGCCCTTTCCTTCATCAGATGACTTCTGTGAAGCTGC            1632
TGCAAGCGACCACGGGAAAGGAAGTAGTCTACTGAAGACACTTCGACG

CTATGTTGAGTGTGTTGAACTAAATGAGCTCTGCTTTGGGTGTCCAGG            1680
GATACAACTCACACAACTTGATTTACTCGAGACGAAACCCACAGGTCC

CCTGGGGTTTGTGCCGCAGTTGGAGCCAGCAGTGACTTCACTCTGACT            1728
GGACCCCAAACACGGCGTCAACCTCGGTCGTCACTGAAGTGAGACTGA

TGGGACTGAGAATGCATTTCCTGGTGGAGACACTCGGGTGCAGAAATA            1776
ACCCTGACTCTTACGTAAAGGACCACCTCTGTGAGCCCACGTCTTTAT

TAACAGAAGGTGACATACATGCTGAAGCTGAGGACTAGGTCGAAAGTT            1824
ATTGTCTTCCACTGTATGTACGACTTCGACTCCTGATCCAGCTTTCAA

AACGACGTTGCATTTTCAGCCTTGGGTATCCTCTCTGCCTGCCAGGAC            1872
TTGCTGCAACGTAAAAGTCGGAACCCATAGGAGAGACGGACGGTCCTG

TCTAGCCAGTGTCTGGTACACACTTCTTGGCATGGACACCTAGGTCGA            1920
AGATCGGTCACAGACCATGTGTGAAGAACCGTACCTGTGGATCCAGCT

CGCGGGCGCGATTCGGCCGACTCGAG                                  1946
GCGCCCGCGCTAAGCCGGCTGAGCTC
```

FIGURE 4D

FIG. 7A
FIG. 7B
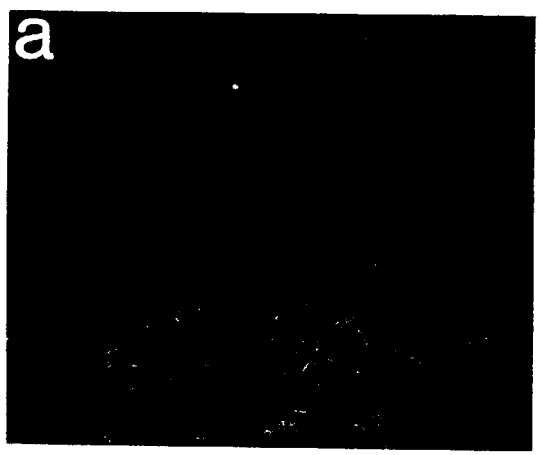
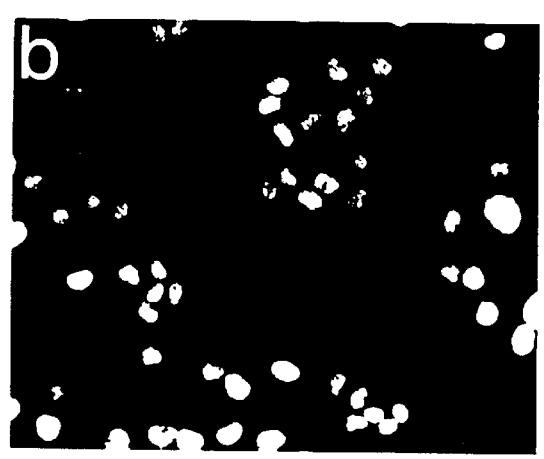

ANTIBODIES FOR NF-AT INTERACTING PROTEIN, NIP45

RELATED APPLICATIONS

This application is a divisional application of U.S. Ser. No. 09/192,611, filed Nov. 16, 1998 (now U.S. Pat. No. 6,090,561) which is a divisional application of U.S. Ser. No. 08/755,584, filed Nov. 25, 1996 (now U.S. Pat. No. 5,858,711), the entire contents of which are expressly incorporated herein by reference.

GOVERNMENT FUNDING

Work described herein was supported, at least in part, under grant AI37833 awarded by the National Institutes of Health. The U.S. government therefore may have certain rights in this invention.

BACKGROUND OF THE INVENTION

CD4+ T helper cells are not a homogeneous population but can be divided on the basis of cytokine secretion into at least two subsets termed T helper type 1 (Th1) and T helper type 2 (Th2) (see e.g., Mosmann, T. R. et al. (1986) *J. Immunol.* 136:2348–2357; Paul, W. E. and Seder, R. A. (1994) *Cell* 76:241–251; Seder, R. A. and Paul, W. E. (1994) *Ann. Rev. Immunol.* 12:635–673). Th1 cells secrete interleukin-2 (IL-2) and interferon-γ (IFN-γ) while Th2 cells produce interleukin-4 (IL-4), interleukin-5 (IL-5), interleukin-10 (IL-10) and interleukin-13 (IL-13). Both subsets produce cytokines such as tumor necrosis factor (TNF) and granulocyte/macrophage-colony stimulating factor (GM-CSF). In addition to their different pattern of cytokine expression, Th1 and Th2 cells are thought to have differing fuctional activities. For example, Th1 cells are involved in inducing delayed type hypersensitivity responses, whereas Th2 cells are involved in providing efficient "help" to B lymphocytes and stimulating production of IgG1 and IgE antibodies.

There is now abundant evidence that the ratio of Th1 to Th2 cells is highly relevant to the outcome of a wide array of immunologically-mediated clinical diseases including autoimmune, allergic and infectious diseases. For example, in experimental leishmania infections in mice, animals that are resistant to infection mount predominantly a Th1 response, whereas animals that are susceptible to progressive infection mount predominantly a Th2 response (Heinzel, F. P., et al. (1989) *J. Exp. Med.* 169:59–72; Locksley, R. M. and Scott, P. (1992) *Immunoparasitology Today* 1:A58–A61). In murine schistosomiasis, a Th1 to Th2 switch is observed coincident with the release of eggs into the tissues by female parasites and is associated with a worsening of the disease condition (Pearce, E. J., et al. (1991) *J. Exp. Med.* 173:159–166; Grzych, J-M., et al. (1991) *J. Immunol.* 141:1322–1327; Kullberg, M. C., et al. (1992) *J. Immunol.* 148:3264–3270). Many human diseases, including chronic infections (such as with human immunodeficiency virus (HIV) and tuberculosis) and certain metastatic carcinomas, also are characterized by a Th1 to Th2 switch (see e.g., Shearer, G. M. and Clerici, M. (1992) *Prog. Chem. Immunol.* 54:21–43; Clerici, M and Shearer, G. M. (1993) *Immunology Today* 14:107–111; Yamamura, M., et al. (1993) *J. Clin. Invest.* 91:1005–1010; Pisa, P., et al. (1992) *Proc. Natl. Acad. Sci. USA* 89:7708–7712; Fauci, A. S. (1988) *Science* 239:617–623). Furthermore, certain autoimmune diseases have been shown to be associated with a predominant Th1 response. For example, patients with rheumatoid arthritis have predominantly Th1 cells in synovial tissue (Simon, A. K., et al. (1994) *Proc. Natl. Acad. Sci. USA* 91:8562–8566) and experimental autoimmune encephalomyelitis (EAE) can be induced by autoreactive Th1 cells (Kuchroo, V. K., et al. (1993) *J. Immunol.* 151:4371–4381).

The ability to alter or manipulate ratios of Th1 and Th2 subsets requires an understanding of the mechanisms by which the differentiation of CD4 T helper precursor cells (Thp), which secrete only IL-2, choose to become Th1 or Th2 effector cells. It is clear that the cytokines themselves are potent Th cell inducers and form an autoregulatory loop (see e.g., Paul, W. E. and Seder, R. A. (1994) *Cell* 76:241–251; Seder, R. A. and Paul, W. E. (1994) *Ann. Rev. Immunol.* 12:635–673). Thus, IL-4 promotes the differentiation of Th2 cells while preventing the differentiation of precursors into Th1 cells, while IL-12 and IFN-γ have the opposite effect. One possible means therefore to alter Th1:Th2 ratios is to increase or decrease the level of selected cytokines. Direct administration of cytokines or antibodies to cytokines has been shown to have an effect on certain diseases mediated by either Th1 or Th2 cells. For example, administration of recombinant IL-4 or antibodies to IL-12 ameliorate EAE, a Th1-driven autoimmune disease (see Racke; M. K. et al. (1994) *J. Exp. Med.* 180:1961–1966; and Leonard, J. P. et al. (1995) *J. Exp. Med.* 181:381–386), while anti-IL-4 antibodies cure the Th2-mediated parasitic disease, *Leishmania major* (Sadick, M. D. et al. (1990) *J. Exp. Med.* 171:115–127). However, as therapeutic options, systemic administration of cytokines or antibodies may have unwanted side effects and, accordingly, alternative approaches to manipulating Th1/Th2 subsets are still needed.

While the molecular basis for the tissue-specific expression of T cell cytokines has remained elusive, study of the transcriptional elements of cytokine genes has provided insight into their regulation. Analysis of the IL-4 cytokine promoter, for example, has revealed functionally critical sites for several transcription factors including members of the NF-AT and AP-1 families (Rooney, J. W. et al. (1995) *Immunity* 2:473–483; Szabo, S. J. et al. (1993) *Mol. Cell. Biol.* 13:4793–4805). NF-AT is a multisubunit transcription complex that contains a cyclosporin A sensitive cytoplasmic phosphoprotein and an inducible nuclear component composed of AP-1 family member proteins (Flanagan, W. M. et al. (1991) *Nature* 352:803–807; Jain, J. et al. (1992) *Nature* 356:801–804). Purification and cloning of NF-ATp revealed a region of limited sequence identity to the Rel Homology Domain (RHD) of the NFκB family of transcription factors (McCaffrey, P. G. et al. (1993) *Science* 262:750–754). Subsequent cloning and sequencing of three related genes, NF-ATc, NF-AT4/x/c3, and NF-AT3/c4 revealed similar domains. NF-AT family members share approximately 70% sequence similarity within this domain and approximately 18% sequence similarity to the RHD of the Rel/NFκB family of transcription factors. Consistent with their very limited sequence similarity in the RHD, there are marked differences in the behavior of NFκB and NF-AT proteins, and much less is known about the pathways that mediate transcriptional regulation of NF-AT target genes. However, considering that NF-AT family members can bind to and transactivate the promoters of multiple cytokine genes including IL-2 and IL-4 (Rooney, J. et al. (1995) *Immunity* 2:545–553; Szabo, S. J. et al. (1993) *Mol. Cell. Biol.* 13:4793–4805; Flanagan, W. M. et al. (1991) *Nature* 352:803–807; Northrop, J. P. et al. (1994) *Nature* 369:497), NF-AT proteins are not likely to be directly responsible for mediating Th1- or Th2-specific cytokine transcription.

Most, if not all, NF-AT binding sites in cytokine promoter regulatory regions are accompanied by nearby sites that bind auxiliary transcription factors, usually members of the AP-1 family. It has been shown that NF-AT and AP-1 proteins bind coordinately and cooperatively and are required for full activity of the IL-2 and IL-4 promoters. Different AP-1 proteins, specifically c-Jun, c-Fos, Fra-1, Fra-2, Jun B and Jun D, have been shown to bind to these sites (Rao, A. et al (1994) *Immunol. Today* 15:274–281; Jain, J. et al. (1993) *Nature* 365:352–355; Boise, L. H. et al (1993) *Mol. Cell. Biol.* 13:1911–1919; Rooney, J. et al. (1995) *Immunity* 2:545–553; Rooney, J. et al. (1995) *Mol. Cell. Biol.* 15:6299–6310). However, none of these AP-1 proteins is expressed in a Th1- or Th2-specific manner and there is no evidence for the differential recruitment of AP-1 family members to the IL-2 or IL-4 composite sites (Rooney, J. et al. (1995) *Mol. Cell. Biol.* 15:6299–6310). Thus, neither NF-AT proteins nor the AP-1 family members c-Jun, c-Fos, Fra-1, Fra-2, Jun B and Jun D can account for the tissue-specific transcription of IL-4 in Th2 cells.

In the related co-pending application U.S. Ser. No. 08/636,602, we have provided evidence that the selective expression of the proto-oncogene c-maf in Th2 cells is responsible for tissue-specific IL-4 expression. Interestingly, c-Maf acts in synergy with NF-AT proteins to transactivate the IL-4 promoter. This is consistent with previous data that the inducible expression of multiple cytokine genes and cell surface proteins following T cell receptor stimulation requires members of the NF-AT transcription factor family (Rooney, J. W. et al. (1995) *Immunity* 2:473–483; Cockerill, P. N. et al. (1995) *Mol. Cell. Biol.* 15:2071–2079; Goldfeld, A. E. et al. (1993) *J. Exp. Med.* 178:1365–1379; Shaw, J. P. et al. (1988) *Science* 241:202–205). However, it was unknown, prior to the present invention, whether additional proteins exist that act in concert with known transcriptional activators, such as NF-AT and c-Maf, to activate cytokine gene expression.

SUMMARY OF THE INVENTION

A 45 kDa protein, termed NIP45, that interacts with members of the NF-AT family of proteins has now been isolated and characterized. NIP45 was isolated based upon its ability to interact with the Rel Homology Domain (RHD) of NF-AT. Furthermore, NIP45 has been shown to synergize with NF-AT and c-Maf to stimulate cytokine gene expression. This invention pertains to isolated compositions of NIP45 protein and isolated nucleic acid sequences encoding NIP45, other compositions related thereto and methods of use thereof. The amino acid sequence of NIP45 protein has been determined (shown in SEQ ID NO: 2) and a cDNA encoding NIP45 protein has been isolated (the nucleotide sequence of which is shown in SEQ ID NO: 1).

One aspect of the invention pertains to isolated nucleic acid molecules encoding NIP45, or fragments thereof. In one embodiment, the invention provides an isolated nucleic acid molecule comprising a nucleotide sequence encoding NIP45 protein. In another embodiment, the invention provides an isolated nucleic acid molecule comprising a nucleotide sequence encoding a protein, wherein the protein comprises an amino acid sequence that is homologous to the amino acid sequence of SEQ ID NO: 2 and interacts with the Rel Homology Domain of an NF-AT family protein. In yet another embodiment, the invention provides an isolated nucleic acid molecule which hybridizes under stringent conditions to a nucleic acid molecule comprising the nucleotide sequence of SEQ ID NO: 1. In yet another embodiment, the invention provides an isolated nucleic acid molecule comprising the nucleotide sequence of SEQ ID NO: 1. In still other embodiments, the invention provides an isolated nucleic acid molecule encoding the amino acid sequence of SEQ ID NO: 2. Isolated nucleic acid molecules encoding NIP45 fusion proteins and isolated antisense nucleic acid molecules are also encompassed by the invention.

Another aspect of the invention pertains to vectors, such as recombinant expression vectors, containing an nucleic acid molecule of the invention and host cells into which such vectors have been introduced. In one embodiment, such a host cell is used to produce NIP45 protein by culturing the host cell in a suitable medium. If desired, NIP45 protein can be then isolated from the host cell or the medium.

Still another aspect of the invention pertains to isolated NIP45 proteins, or portions thereof. In one embodiment, the invention provides an isolated NIP45 protein, or a portion thereof that interacts with an NF-AT family protein. In yet another embodiment, the invention provides an isolated protein which comprises an amino acid sequence homologous to the amino acid sequence of SEQ ID NO: 2 and that interacts with an NF-AT family protein. NIP45 fusion proteins are also encompassed by the invention.

The NIP45 proteins of the invention, or fragments thereof, can be used to prepare anti-NIP45 antibodies. Accordingly, the invention further provides an antibody that specifically binds NIP45 protein. In one embodiment, the antibody is monoclonal. In another embodiment, the antibody is labeled with a detectable substance.

The NIP45-encoding nucleic acid molecules of the invention can be used to prepare nonhuman transgenic animals that contain cells carrying a transgene encoding NIP45 protein or a portion of NIP45 protein. Accordingly, such transgenic animals are also provided by the invention. In one embodiment, the NIP45 transgene carried by the transgenic animal alters an endogenous gene encoding endogenous NIP45 protein (e.g., a homologous recombinant animal).

Another aspect of the invention pertains to methods for detecting the presence of NIP45 protein or mRNA in a biological sample. To detect NIP45 protein or mRNA, the biological sample is contacted with an agent capable of detecting NIP45 protein (such as a labeled anti-NIP45 antibody) or NIP45 mRNA (such as a labeled nucleic acid probe capable of hybridizing to NIP45 mRNA) such that the presence of NIP45 protein or mRNA is detected in the biological sample.

Still another aspect of the invention pertains to methods for identifying compounds that modulate the activity or expression of NIP45 and methods for identifying compounds that modulate an interaction between NIP45 and an NF-AT family protein. Screening metods for identifying proteins that interact with NIP45 are also encompassed by the invention.

BRIEF DESCRIPTION OF THE DRAWINGS

FIG. 4 depicts the nucleotide (SEQ ID NO:1) and predicted amino acid sequences (SEQ ID NO:2) of the original NIP45 cDNA isolate.

FIG. 7A is a photograph of immunofluorescence analysis of BHK cells transfected with an expression construct encoding an HA-epitope tagged NIP45 protein and probed with a monoclonal antibody specific for the HA peptide as the primary antibody and an indocarbocyanine labelled goat anti-mouse secondary reagent.

FIG. 7B is a photograph of the same cells depicted in FIG. 7A counterstained with the DNA staining dye Hoechst 33258.

DETAILED DESCRIPTION OF THE INVENTION

Figure 1:
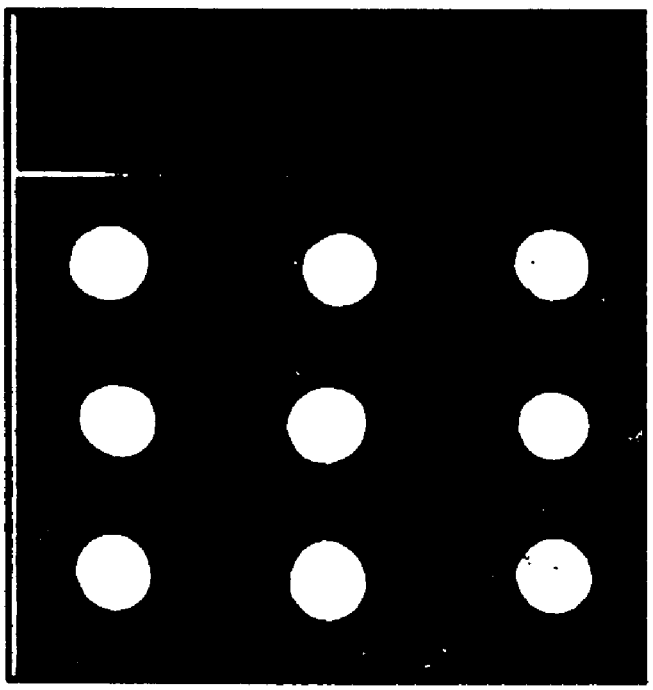
FIG. 1 is photograph of yeast colonies, in triplicate, transformed with the NIP45 plasmid and either NF-ATp-RHD as "bait" or control baits, Max, CDK2 or pEG202, together with the LacZ reporter plasmid pSH18, indicating that only those colonies containing the NIP45 plasmid and the NF-ATp-RHD bait expressed the LacZ reporter gene.

This invention pertains to NF-AT Interacting Protein 45 (NIP45), a 45 kDa protein that interacts with NF-AT proteins. A cDNA encoding NIP45 was isolated based upon the interaction of NIP45 with the RHD of NF-ATp using a two-hybrid interaction trap assay in yeast (see Example 1). Coimmunoprecipitation experiments demonstrated that NIP45 and NF-AT interact in vivo in mammalian cells (see Example 2). The cDNA encoding NIP45 has been sequenced and characterized (see Example 3). Examination of the tissue expression pattern of NIP45 mRNA revealed that the NIP45 transcript is preferentially expressed in spleen, thymus and testis (see Example 4). Subcellular localization studies demonstrated that NIP45 protein is evenly distributed throughout the cell nucleus (see Example 5). Functional studies showed that NIP45 synergizes with NF-AT to stimulate transcription from promoters containing NF-AT binding sites and, moreover, synergizes with NF-AT and c-Maf to stimulate transcription from the IL-4 promoter (see Example 6). Moreover, NIP45, NF-AT and c-Maf can act in concert to induce expression of the endogenous IL-4 gene in cells that do not normally express IL-4 (e.g., B cells.) (see Example 7).

So that the invention may be more readily understood, certain terms are first defined.

As used herein, the term "NF-AT family protein" (also referred to interchangeably as simple "NF-AT") refers to the family of Nuclear Factors of Activated T cell transcription factors, including NF-ATp, NF-ATc, NF-AT4/x/c3 and NF-AT3/c4.

As used herein the term "Rel Homology Domain of an NF-AT family protein" (abbreviated as RHD domain) refers to a domain within NF-AT family proteins having approximately 70% sequence similarity within the RHD of the Rel/NFκB family of transcription factors.

As used herein, the term "nucleic acid molecule" is intended to include DNA molecules (e.g., cDNA or genomic DNA) and RNA molecules (e.g., mRNA). The nucleic acid molecule may be single-stranded or double-stranded, but preferably is double-stranded DNA.

An used herein, an "isolated nucleic acid molecule" refers to a nucleic acid molecule that is free of gene sequences which naturally flank the nucleic acid in the genomic DNA of the organism from which the nucleic acid is derived (i.e., gene sequences that are located adjacent to the isolated nucleic molecule in the genomic DNA of the organism from which the nucleic acid is derived). For example, in various embodiments, the isolated NIP45 nucleic acid molecule may contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, may be free of other cellular material.

As used herein, the term "hybridizes under stringent conditions" is intended to describe conditions for hybridization and washing under which nucleotide sequences at least 60% homologous to each other typically remain hybridized to each other. Preferably, the conditions are such that at least sequences at least 65%, more preferably at least 70%, and even more preferably at least 75% homologous to each other typically remain hybridized to each other. Such stringent conditions are known to those skilled in the art and can be found in Current Protocols in Molecular Biology, John Wiley & Sons, N.Y. (1989), 6.3.1–6.3.6. A preferred, non-limiting example of stringent hybridization conditions are hybridization in 6×sodium chloride/sodium citrate (SSC) at about 45° C., followed by one or more washes in 0.2×SSC, 0.1% SDS at 50–65° C.

As used herein, a "naturally-occurring" nucleic acid molecule refers to an RNA or DNA molecule having a nucleotide sequence that occurs in nature (e.g., encodes a natural protein).

As used herein, an "antisense" nucleic acid comprises a nucleotide sequence which is complementary to a "sense"

nucleic acid encoding a protein, e.g., complementary to the coding strand of a double-stranded cDNA molecule, complementary to an mRNA sequence or complementary to the coding strand of a gene. Accordingly, an antisense nucleic acid can hydrogen bond to a sense nucleic acid.

As used herein, the term "coding region" refers to regions of a nucleotide sequence comprising codons which are translated into amino acid residues, whereas the term "non-coding region" refers to regions of a nucleotide sequence that are not translated into amino acids (e.g., 5' and 3' untranslated regions).

As used herein, the term "vector" refers to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" or simply "expression vectors". In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

As used herein, the term "host cell" is intended to refer to a cell into which a nucleic acid of the invention, such as a recombinant expression vector of the invention, has been introduced. The terms "host cell" and "recombinant host cell" are used interchangeably herein. It should be understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

As used herein, a "transgenic animal" refers to a non-human animal, preferably a mammal, more preferably a mouse, in which one or more of the cells of the animal includes a "transgene". The term "transgene" refers to exogenous DNA which is integrated into the genome of a cell from which a transgenic animal develops and which remains in the genome of the mature animal, for example directing the expression of an encoded gene product in one or more cell types or tissues of the transgenic animal.

As used herein, a "homologous recombinant animal" refers to a type of transgenic non-human animal, preferably a mammal, more preferably a mouse, in which an endogenous gene has been altered by homologous recombination between the endogenous gene and an exogenous DNA molecule introduced into a cell of the animal, e.g., an embryonic cell of the animal, prior to development of the animal.

As used herein, an "isolated protein" refers to a protein that is substantially free of cellular material or culture medium when isolated from cells or produced by recombinant DNA techniques, or chemical precursors or other chemicals when chemically synthesized.

As used herein, the term "antibody" is intended to include immunoglobulin molecules and immunologically active portions of immunoglobulin molecules, i.e., molecules that contain an antigen binding site which specifically binds (immunoreacts with) an antigen, such as Fab and F(ab')$_2$ fragments. The terms "monoclonal antibody" and "monoclonal antibody composition", as used herein, refer to a population of antibody molecules that contain only one species of an antigen binding site capable of immunoreacting with a particular epitope of an antigen. A monoclonal antibody composition thus typically displays a single binding affinity for a particular antigen with which it immunoreacts.

Various aspects of the invention are described in further detail in the following subsections:

I. Isolated Nucleic Acid Molecules

One aspect of the invention pertains to isolated nucleic acid molecules that encode NIP45, or fragments thereof. In a preferred embodiment, an isolated nucleic acid molecule of the invention comprises the nucleotide sequence shown in SEQ ID NO: 1. The sequence of SEQ ID NO: 1 corresponds to the mouse NIP45 cDNA. This cDNA comprises sequences encoding the NIP45 protein (i.e., "the coding region", from nucleotides 13–1248), as well as 5' untranslated sequences (nucleotides 1–12) and 3' untranslated sequences (nucleotides 1249–1946). Alternatively, the nucleic acid molecule may comprise only the coding region of SEQ ID NO: 1 (i.e., nucleotides 13–1248).

Moreover, the nucleic acid molecule of the invention can comprise only a portion of the coding region of SEQ ID NO: 1, for example a fragment encoding a biologically active portion of NIP45. The term "biologically active portion of NIP45" is intended to include portions of NIP45 that retain the ability to interact with the RHD of NF-AT family proteins. The ability of portions of NIP45 to interact with an NF-AT RHD can be determined in standard in vitro interaction assays, for example using a NF-AT RHD fusion protein. Nucleic acid fragments encoding biologically active portions of NIP45 can be prepared by isolating a portion of SEQ ID NO: 1, expressing the encoded portion of NIP45 protein or peptide (e.g., by recombinant expression in a host cell) and assessing the ability of the portion to interact with NF-AT, in particular the NF-AT RHD, for example using a glutathione-S-transferase (GST)-NF-AT RHD fusion protein.

The invention further encompasses nucleic acid molecules that differ from SEQ ID NO: 1 (and fragments thereof) due to degeneracy of the genetic code and thus encode the same NIP45 protein as that encoded by SEQ ID NO: 1. Accordingly, in another embodiment, an isolated nucleic acid molecule of the invention has a nucleotide sequence encoding a protein having an amino acid sequence shown in SEQ ID NO: 2. Moreover, the invention encompasses nucleic acid molecules that encode portions of SEQ ID NO: 2, such as biologically active portions thereof.

A nucleic acid molecule having the nucleotide sequence of SEQ ID NO: 1, or a portion thereof, can be isolated using standard molecular biology techniques and the sequence information provided herein. For example, a NIP45 cDNA can be isolated from a cDNA library using all or portion of SEQ ID NO: 1 as a hybridization probe and standard hybridization techniques (e.g., as described in Sambrook, J., et al. *Molecular Cloning: A Laboratory Manual. 2nd, ed.,* Cold Spring Harbor Laboratory, Cold Spring Harbor, N.Y., 1989). Moreover, a nucleic acid molecule encompassing all or a portion of SEQ ID NO: 1 can be isolated by the polymerase chain reaction using oligonucleotide primers designed based upon the sequence of SEQ ID NO: 1. For example, mRNA can be isolated from cells (e.g., by the guanidinium-thiocyanate extraction procedure of Chirgwin et al. (1979) *Biochemistry* 18: 5294–5299) and cDNA can be prepared using reverse transcriptase (e.g., Moloney MLV reverse transcriptase, available from Gibco/BRL, Bethesda, Md.; or AMV reverse transcriptase, available from Seikagaku America, Inc., St. Petersburg, Fla.). Synthetic oligonucleotide primers for PCR amplification can be designed based upon the nucleotide sequence shown in SEQ ID NO: 1. A nucleic acid of the invention can be amplified using cDNA or, alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to a NIP45 nucleotide sequence can be prepared by standard synthetic techniques, e.g., using an automated DNA synthesizer.

In addition to the NIP45 nucleotide sequence shown in SEQ ID NO: 1, it will be appreciated by those skilled in the art that DNA sequence polymorphisms that lead to changes in the amino acid sequences of NIP45 may exist within a population. Such genetic polymorphism in the NIP45 gene may exist among individuals within a population due to natural allelic variation. Such natural allelic variations can typically result in 1–5% variance in the nucleotide sequence of the a gene. Any and all such nucleotide variations and resulting amino acid polymorphisms in NIP45 that are the result of natural allelic variation and that do not alter the functional activity of NIP45 are intended to be within the scope of the invention. Moreover, nucleic acid molecules encoding NIP45 proteins from other species, and thus which have a nucleotide sequence that differs from the mouse sequence of SEQ ID NO: 1 but that is related to the mouse sequence, are intended to be within the scope of the invention. Nucleic acid molecules corresponding to natural allelic variants and human and other mammalian homologues of the mouse NIP45 cDNA of the invention can be isolated based on their homology to the mouse NIP45 nucleic acid molecule disclosed herein using the mouse cDNA, or a portion thereof, as a hybridization probe according to standard hybridization techniques under stringent hybridization conditions. Accordingly, in another embodiment, an isolated nucleic acid molecule of the invention hybridizes under stringent conditions to the nucleic acid molecule comprising the nucleotide sequence of SEQ ID NO: 1. In certain embodiment, the nucleic acid is at least 15, 30, 50, 100, 200, 300, 400, 500, 600, 700, 800, 900, 1000 or 1500 nucleotides in length. Preferably, an isolated nucleic acid molecule of the invention that hybridizes under stringent conditions to the sequence of SEQ ID NO: 1 corresponds to a naturally-occurring nucleic acid molecule. In on embodiment, the nucleic acid encodes natural human NIP45 protein. In another embodiment, the nucleic acid molecule encodes a murine NIP45 protein, such as mouse NIP45 protein.

In addition to naturally-occurring allelic variants of the NIP45 sequence that may exist in the population, the skilled artisan will further appreciate that changes may be introduced by mutation into the nucleotide sequence of SEQ ID NO: 1, thereby leading to changes in the amino acid sequence of the encoded protein, without altering the functional activity of the NIP45 protein. For example, nucleotide substitutions leading to amino acid substitutions at "non-essential" amino acid residues may be made in the sequence of SEQ ID NO: 1. A "non-essential" amino acid residue is a residue that can be altered from the wild-type sequence of NIP45 (e.g., the sequence of SEQ ID NO: 2) without altering the functional activity of NIP45, such as its ability to interact with an NF-AT RHD or its ability to synergize with NF-AT and c-Maf in stimulating gene transcription, whereas an "essential" amino acid residue is required for functional activity.

Accordingly, another aspect of the invention pertains to nucleic acid molecules encoding NIP45 proteins that contain changes in amino acid residues that are not essential for NIP45 activity. Such NIP45 proteins differ in amino acid sequence from SEQ ID NO: 2 yet retain NIP45 activity. In one embodiment, the isolated nucleic acid molecule comprises a nucleotide sequence encoding a protein, wherein the protein comprises an amino acid sequence at least 60% homologous to the amino acid sequence of SEQ ID NO: 2 and interacts with the RHD of an NF-AT family protein. Preferably, the protein encoded by the nucleic acid molecule is at least 70% homologous to SEQ ID NO: 2, more preferably at least 80% homologous to SEQ ID NO: 2, even more preferably at least 90% homologous to SEQ ID NO: 2, and most preferably at least 95% homologous to SEQ ID NO: 2.

To determine the percent homology of two amino acid sequences (e.g., SEQ ID NO: 2 and a mutant form thereof), the sequences are aligned for optimal comparison purposes (e.g., gaps may be introduced in the sequence of one protein for optimal alignment with the other protein). The amino acid residues at corresponding amino acid positions are then compared. When a position in one sequence (e.g., SEQ ID NO: 2) is occupied by the same amino acid residue as the corresponding position in the other sequence (e.g., a mutant form of NIP45), then the molecules are homologous at that position (i.e., as used herein amino acid "homology" is equivalent to amino acid "identity"). The percent homology between the two sequences is a function of the number of identical positions shared by the sequences (i.e., % homology=# of identical positions/total # of positions×100).

An isolated nucleic acid molecule encoding a NIP45 protein homologous to the protein of SEQ ID NO: 2 can be created by introducing one or more nucleotide substitutions, additions or deletions into the nucleotide sequence of SEQ ID NO: 1 such that one or more amino acid substitutions, additions or deletions are introduced into the encoded protein. Mutations can be introduced into SEQ ID NO: 1 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, an amino acid residue in NIP45 protein is preferably replaced with another amino acid residue from the same side chain family. Alternatively, in another embodiment, mutations can be introduced randomly along all or part of a NIP45 coding sequence, such as by saturation mutagenesis, and the resultant mutants can be screened for their ability to interact with an NF-AT RHD (e.g., using a GST-NF-AT-RHD fusion protein) to identify mutants that retain NF-AT-interacting ability. Following mutagenesis of SEQ ID NO: 1, the encoded mutant protein can be expressed recombinantly in a host cell and the ability of the mutant protein to interact with NF-AT can be determined using an in vitro interaction assay. For example, a recombinant NIP45 protein (e.g., a mutated or truncated form of SEQ ID NO: 2) can be radiolabeled and incubated with a GST-NF-AT RHD fusion protein. Glutathione-sepharose beads are then added to the mixture to precipitate the NIP45-GST-NF-AT RHD complex, if such a complex is formed. After washing the beads to remove non-specific binding, the amount of radioactive protein associated with the beads is determined and compared to the amount of radioactive protein remaining in the eluate to thereby determine whether the NIP45 protein is capable of interacting with the RHD of NF-AT.

Another aspect of the invention pertains to isolated nucleic acid molecules that are antisense to the coding strand of a NIP45 mRNA or gene. An antisense nucleic acid of the invention can be complementary to an entire NIP45 coding strand, or to only a portion thereof. In one embodiment, an antisense nucleic acid molecule is antisense to a coding region of the coding strand of a nucleotide sequence encoding NIP45 (e.g., the entire coding region of SEQ ID NO: 1 comprises nucleotides 13–1248). In another embodiment, the antisense nucleic acid molecule is antisense to a non-coding region of the coding strand of a nucleotide sequence encoding NIP45. In certain embodiments, an antisense nucleic acid of the invention is at least 15, 30, 50, 100, 200, 300, 400, 500, 600, 700, 800, 900, 1000 or 1500 nucleotides in length.

Given the coding strand sequences encoding NIP45 disclosed herein (e.g., SEQ ID NO: 1), antisense nucleic acids of the invention can be designed according to the rules of Watson and Crick base pairing. The antisense nucleic acid molecule may be complementary to the entire coding region of NIP45 mRNA, or alternatively can be an oligonucleotide which is antisense to only a portion of the coding or noncoding region of NIP45 mRNA. For example, the antisense oligonucleotide may be complementary to the region surrounding the translation start site of NIP45 mRNA. An antisense oligonucleotide can be, for example, about 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

In another embodiment, an antisense nucleic acid of the invention is a ribozyme.

Ribozymes are catalytic RNA molecules with ribonuclease activity which are capable of cleaving a single-stranded nucleic acid, such as an mRNA, to which they have a complementary region. A ribozyme having specificity for a NIP45-encoding nucleic acid can be designed based upon the nucleotide sequence of a NIP45 cDNA disclosed herein (i.e., SEQ ID NO: 1). For example, a derivative of a Tetrahymena L-19 IVS RNA can be constructed in which the base sequence of the active site is complementary to the base sequence to be cleaved in a NIP45-encoding mRNA. See for example Cech et al. U.S. Pat. No. 4,987,071; and Cech et al. U.S. Pat. No. 5,116,742. Alternatively, NIP45 mRNA can be used to select a catalytic RNA having a specific ribonuclease activity from a pool of RNA molecules. See for example Bartel, D. and Szostak, J. W. (1993) *Science* 261: 1411–1418.

Yet another aspect of the invention pertains to isolated nucleic acid molecules encoding NIP45 fusion proteins. Such nucleic acid molecules, comprising at least a first nucleotide sequence encoding a NIP45 protein, polypeptide or peptide operatively linked to a second nucleotide sequence encoding a non-NIP45 protein, polypeptide or peptide, can be prepared by standard recombinant DNA techniques. NIP45 fusion proteins are described in further detail below in subsection III.

II. Recombinant Expression Vectors and Host Cells

Another aspect of the invention pertains to vectors, preferably recombinant expression vectors, containing a nucleic acid encoding NIP45 (or a portion thereof). The expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to includes promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector may depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., NIP45 proteins, mutant forms of NIP45 proteins, NIP45 fusion proteins and the like).

The recombinant expression vectors of the invention can be designed for expression of NIP45 protein in prokaryotic or eukaryotic cells. For example, NIP45 can be expressed in bacterial cells such as *E. coli*, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector may be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Examples of suitable inducible non-fusion *E. coli* expression vectors include pTrc (Amann et al., (1988) *Gene* 69:301–315) and pET 11d (Studier et al., *Gene Expression Technology: Methods in Enzymology* 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174 (DE3) from a resident λ prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada et al., (1992) *Nuc. Acids Res.* 20:2111–2118). Such alteration of nucleic acid sequences of the invention can be carried out by standard DNA synthesis techniques.

In another embodiment, the NIP45 expression vector is a yeast expression vector. Examples of vectors for expression in yeast *S. cerivisae* include pYepSec1 (Baldari. et al., (1987) *EMBO J.* 6:229–234), pMFa (Kurjan and Herskowitz, (1982) *Cell* 30:933–943), pJRY88 (Schultz et al., (1987) *Gene* 54:113–123), and pYES2 (Invitrogen Corporation, San Diego, Calif.).

Alternatively, NIP45 can be expressed in insect cells using baculovirus expression vectors. Baculovirus vectors available for expression of proteins in cultured insect cells (e.g., Sf 9 cells) include the pAc series (Smith et al., (1983) *Mol. Cell Biol.* 3:2156–2165) and the pVL series (Lucklow, V. A., and Summers, M. D., (1989) *Virology* 170:31–39).

In yet another embodiment, a nucleic acid of the invention is expressed in mammalian cells using a mammalian expression vector. Examples of mammalian expression vectors include pMex-NeoI, pCDM8 (Seed, B., (1987) *Nature* 329:840) and pMT2PC (Kaufman et al. (1987), *EMBO J.* 6:187–195). When used in mammalian cells, the expression vector's control functions are often provided by viral regulatory elements. For example, commonly used promoters are derived from polyoma, Adenovirus 2, cytomegalovirus and Simian Virus 40.

In another embodiment, the recombinant mammalian expression vector is capable of directing, expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji et al. (1983) *Cell* 33:729–740; Queen and Baltimore (1983) *Cell* 33:741–748), the albumin promoter (liver-specific; Pinkert et al. (1987) *Genes Dev.* 1:268–277), neuron-specific promoters (e.g., the neurofilament promoter; Byrne and Ruddle (1989) *Proc. Natl. Acad Sci. USA* 86:5473–5477), pancreas-specific promoters (Edlund et al. (1985) *Science* 230:912–916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374–379) and the α-fetoprotein promoter (Campes and Tilghman (1989) *Genes Dev.* 3:537–546).

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to NIP45 mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, *Reviews—Trends in Genetics*, Vol. 1(1) 1986.

Another aspect of the invention pertains to recombinant host cells into which a vector, preferably a recombinant expression vector, of the invention has been introduced. A host cell may be any prokaryotic or eukaryotic cell. For example, NIP45 protein may be expressed in bacterial cells such as *E. coli*, insect cells, yeast or mammalian cells (such as Chinese hamster ovary cells (CHO) or COS cells). Other suitable host cells are known to those skilled in the art. Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook et al. (*Molecular Cloning: A Laboratory Manual,* 2nd Edition, Cold Spring Harbor Laboratory press (1989)), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker may be introduced into a host cell on the same vector as that encoding NIP45 or may be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) NIP45 protein. Accordingly, the invention further provides methods for producing NIP45 protein using the host cells of the invention. In one embodiment, the method comprises culturing the host cell of invention (into which a recombinant expression vector encoding NIP45 has been introduced) in a suitable medium until NIP45 is produced. In another embodiment, the method further comprises isolating NIP45 from the medium or the host cell. In its native form NIP45 protein is an intracellular protein and, accordingly, recombinant NIP45 protein can be expressed intracellularly in a recombinant host cell and then isolated from the host cell, e.g., by lysing the host cell and recovering the recombinant NIP45 protein from the lysate. Alternatively, recombinant NIP45 protein can be prepared as a extracellular protein by operatively linking a heterologous signal sequence to the amino-terminus of the protein such that the protein is secreted from the host cells. In this case, recombinant NIP45 protein can be recovered from the culture medium in which the cells are cultured.

Certain host cells of the invention can also be used to produce nonhuman transgenic animals. For example, in one embodiment, a host cell of the invention is a fertilized oocyte or an embryonic stem cell into which NIP45-coding sequences have been introduced. Such host cells can then be used to create non-human transgenic animals in which exogenous NIP45 sequences have been introduced into their genome or homologous recombinant animals in which endogenous NIP45 sequences have been altered. Such animals are useful for studying the function and/or activity of NIP45 and for identifying and/or evaluating modulators of NIP45 activity. Accordingly, another aspect of the invention pertains to nonhuman transgenic animals which contain cells carrying a transgene encoding a NIP45 protein or a portion of a NIP45 protein. In a subembodiment, of the transgenic animals of the invention, the transgene alters an endogenous gene encoding an endogenous NIP45 protein (e.g., homologous recombinant animals in which the endogenous NIP45 gene has been functionally disrupted or "knocked out", or the nucleotide sequence of the endogenous NIP45 gene has been mutated or the transcriptional regulatory region of the endogenous NIP45 gene has been altered).

A transgenic animal of the invention can be created by introducing NIP45-encoding nucleic acid into the male pronuclei of a fertilized oocyte, e.g., by microinjection, and allowing the oocyte to develop in a pseudopregnant female foster animal. The mouse NIP45 cDNA sequence of SEQ ID NO: 1 can be introduced as a transgene into the genome of a non-human animal (e.g., a mouse). Alternatively, a mammalian homologue of the mouse NIP45 gene, such as a human NIP45 gene, can be isolated based on hybridization to the mouse NIP45 cDNA and used as a transgene. Intronic sequences and polyadenylation signals can also be included in the transgene to increase the efficiency of expression of the transgene. A tissue-specific regulatory sequence(s) can be operably linked to the NIP45 transgene to direct expression of NIP45 protein to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo,* (Cold Spring Harbor Laboratory Press, Cold Spring Harbor, N.Y., 1986). Similar methods are used for production of other transgenic animals. A transgenic founder animal can be identified based upon the presence of the NIP45 transgene in its genome and/or expression of NIP45 mRNA in tissues or cells of the animals. A transgenic founder animal can then be used to breed additional animals carrying the transgene. Moreover, transgenic animals carrying a transgene encoding NIP45 can further be bred to other transgenic animals carrying other transgenes.

To create a homologous recombinant animal, a vector is prepared which contains at least a portion of a NIP45 gene into which a deletion, addition or substitution has been introduced to thereby alter, e.g., functionally disrupt, the endogenous NIP45 gene. The NIP45 gene preferably is a mouse NIP45 gene. For example, a mouse NIP45 gene can be isolated from a mouse genomic DNA library using the mouse NIP45 cDNA of SEQ ID NO: 1 as a probe. The mouse NIP45 gene then can be used to construct a homologous recombination vector suitable for altering an endogenous NIP45 gene in the mouse genome. In a preferred embodiment, the vector is designed such that, upon homologous recombination, the endogenous NIP45 gene is functionally disrupted (i.e., no longer encodes a functional protein; also referred to as a "knock out" vector). Alternatively, the vector can be designed such that, upon homologous recombination, the endogenous NIP45 gene is mutated or otherwise altered but still encodes functional protein (e.g., the upstream regulatory region can be altered to thereby alter the expression of the endogenous NIP45 protein). In the homologous recombination vector, the altered portion of the NIP45 gene is flanked at its 5' and 3' ends by additional nucleic acid of the NIP45 gene to allow for homologous recombination to occur between the exogenous NIP45 gene carried by the vector and an endogenous NIP45 gene in an embryonic stem cell. The additional flanking NIP45 nucleic acid is of sufficient length for successful homologous recombination with the endogenous gene. Typically, several kilobases of flanking DNA (both at the 5' and 3' ends) are included in the vector (see e.g., Thomas, K. R. and Capecchi, M. R. (1987) *Cell* 51:503 for a description of homologous recombination vectors). The vector is introduced into an embryonic stem cell line (e.g., by electroporation) and cells in which the introduced NIP45 gene has homologously recombined with the endogenous NIP45 gene are selected (see e.g., Li, E. et al. (1992) *Cell* 69:915). The selected cells are then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, A. (1991) *Current Opinion in Biotechnology* 2:823–829 and in PCT International Publication Nos.: WO 90/11354 by Le Mouellec et al.; WO 91/01140 by Smithies et al.; WO 92/0968 by Zijlstra et al.; and WO 93/04169 by Berns et al.

III. Isolated NIP45 Proteins and Anti-NIP45 Antibodies

Another aspect of the invention pertains to isolated NIP45 proteins, and portions thereof, such as biologically active portions, as well as peptide fragments suitable as immunogens to raise anti-NIP45 antibodies. In one embodiment, the invention provides an isolated preparation of NIP45 protein. Preferably, the NIP45 protein has an amino acid sequence shown in SEQ ID NO: 2. In other embodiments, the NIP45 protein is substantially homologous to SEQ ID NO: 2 and retains the functional activity of the protein of SEQ ID NO: 2 yet differs in amino acid sequence due to natural allelic variation or mutagenesis, or is a mammalian homologue of the protein of SEQ ID NO: 2 (e.g., a human homologue), as described in detail in subsection I above. Accordingly, in another embodiment, the NIP45 protein is a protein which comprises an amino acid sequence at least 60% homologous to the amino acid sequence of SEQ ID NO: 2 and that interacts with the RHD of an NF-AT family protein. Preferably, the protein is at least 70% homologous to SEQ ID NO: 2, more preferably at least 80% homologous to SEQ ID NO: 2, even more preferably at least 90% homologous to SEQ ID NO: 2, and most preferably at least 95% homologous to SEQ ID NO: 2.

In other embodiments, the invention provides isolated portions of the NIP45 protein. For example, the invention further encompasses a portion of a NIP45 protein that interacts with NF-AT. As demonstrated in the examples, NIP45 protein interacts with the RHD of NF-AT. An in vitro interaction assay (such as that described above in subsection I utilizing a GST-NF-AT RHD fusion protein) can be used to determine the ability of NIP45 peptide fragments to interact with the NF-AT Rel Homology Domain to thereby identify peptide fragments that interact with NF-AT.

NIP45 proteins are preferably produced by recombinant DNA techniques. For example, a nucleic acid molecule encoding the protein is cloned into an expression vector (as described above), the expression vector is introduced into a host cell (as described above) and the NIP45 protein is expressed in the host cell. The NIP45 protein can then be isolated from the cells by an appropriate purification scheme using standard protein purification techniques. Alternative to recombinant expression, a NIP45 polypeptide can be synthesized chemically using standard peptide synthesis techniques. Moreover, native NIP45 protein can be isolated from cells (e.g., from T cells), for example by immunoprecipitation using an anti-NIP45 antibody.

The invention also provides NIP45 fusion proteins. As used herein, a NIP45 "fusion protein" comprises a NIP45 polypeptide operatively linked to a non-NIP45 polypeptide. A "NIP45 polypeptide" refers to a polypeptide having an amino acid sequence corresponding to NIP45 protein, or a peptide fragment thereof, whereas a "non-NIP45 polypeptide" refers to a polypeptide having an amino acid sequence corresponding to another protein. Within the fusion protein, the term "operatively linked" is intended to indicate that the NIP45 polypeptide and the non-NIP45 polypeptide are fused in-frame to each other. The non-NIP45 polypeptide may be fused to the N-terminus or C-terminus of the NIP45 polypeptide. For example, in one embodiment, the fusion protein is a GST-NIP45 fusion protein in which the NIP45 sequences are fused to the C-terminus of the GST sequences. In another embodiment, the fusion protein is a NIP45-HA fusion protein in which the NIP45 nucleotide sequence is inserted in to the pCEP4-HA vector (Herrscher, R. F. et al. (1995) *Genes Dev.* 9:3067–3082) such that the NIP45 sequences are fused in frame to an influenza hemagglutinin epitope tag. Such fusion proteins can facilitate the purification of recombinant NIP45.

Preferably, a NIP45 fusion protein of the invention is produced by standard recombinant DNA techniques. For example, DNA fragments coding for the different polypeptide sequences are ligated together in-frame in accordance with conventional techniques, for example employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide or an HA epitope tag). A NIP45-encoding nucleic acid can be cloned into such an expression vector such that the fusion moiety is linked in-frame to the NIP45 protein.

Figure 5:
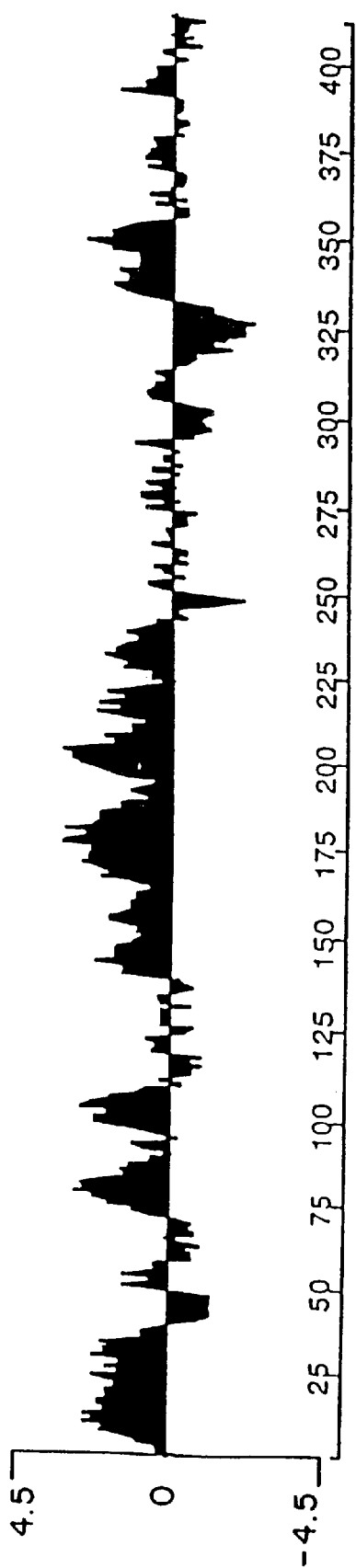
FIG. 5 depicts the hydrophobicity plot of the NIP45 cDNA.

An isolated NIP45 protein, or fragment thereof, can be used as an immunogen to generate antibodies that bind NIP45 using standard techniques for polyclonal and monoclonal antibody preparation. The NIP45 protein can be used to generate antibodies or, alternatively, an antigenic peptide fragment of NIP45 can be used as the immunogen. An antigenic peptide fragment of NIP45 typically comprises at least 8 amino acid residues of the amino acid sequence shown in SEQ ID NO: 2 and encompasses an epitope of NIP45 such that an antibody raised against the peptide forms a specific immune complex with NIP45. Preferably, the antigenic peptide comprises at least 10 amino acid residues, more preferably at least 15 amino acid residues, even more preferably at least 20 amino acid residues, and most preferably at least 30 amino acid residues. Preferred epitopes encompassed by the antigenic peptide are regions of NIP45 that are located on the surface of the protein, e.g., hydrophilic regions. A hydrophobicity analysis of the NIP45 protein sequence of SEQ ID NO: 2 is shown in FIG. 5.

A NIP45 immunogen typically is used to prepare antibodies by immunizing a suitable subject, (e.g., rabbit, goat, mouse or other mammal) with the immunogen. An appropriate immunogenic preparation can contain, for examples, recombinantly expressed NIP45 protein or a chemically synthesized NIP45 peptide. The preparation can further include an adjuvant, such as Freund's complete or incomplete adjuvant, or similar immunostimulatory agent. Immunization of a suitable subject with an immunogenic NIP45 preparation induces a polyclonal anti-NIP45 antibody response.

Accordingly, another aspect of the invention pertains to anti-NIP45 antibodies. Polyclonal anti-NIP45 antibodies can be prepared as described above by immunizing a suitable subject with a NIP45 immunogen. The anti-NIP45 antibody titer in the immunized subject can be monitored over time by standard techniques, such as with an enzyme linked immunosorbent assay (ELISA) using immobilized NIP45. If desired, the antibody molecules directed against NIP45 can be isolated from the mammal (e.g., from the blood) and further purified by well known techniques, such as protein A chromatography to obtain the IgG fraction. At an appropriate time after immunization, e.g., when the anti-NIP45 antibody titers are highest, antibody-producing cells can be obtained from the subject and used to prepare monoclonal antibodies by standard techniques, such as the hybridoma technique originally described by Kohler and Milstein (1975, *Nature* 256:495–497) (see also, Brown et al. (1981) *J. Immunol* 127:539–46; Brown et al. (1980) *J Biol Chem* 255:4980–83; Yeh et al. (1976) *PNAS* 76:2927–31; and Yeh et al. (1982) *Int. J. Cancer* 29:269–75), the more recent human B cell hybridoma technique (Kozbor et al. (1983) *Immunol Today* 4:72), the EBV-hybridoma technique (Cole et al. (1985), *Monoclonal Antibodies and Cancer Therapy*, Alan R. Liss, Inc., pp. 77–96) or trioma techniques. The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) *Yale J. Biol. Med.*, 54:387–402; M. L. Gefter et al. (1977) *Somatic Cell Genet.*, 3:231–36). Briefly, an immortal cell line (typically a myeloma) is fused to lymphocytes (typically splenocytes) from a mammal immunized with a NIP45 immunogen as described above, and the culture supernatants of the resulting hybridoma cells are screened to identify a hybridoma producing a monoclonal antibody that binds NIP45.

Any of the many well known protocols used for fusing lymphocytes and immortalized cell lines can be applied for the purpose of generating an anti-NIP45 monoclonal antibody (see, e.g., G. Galfre et al. (1977) *Nature* 266:55052; Gefter et al. *Somatic Cell Genet.*, cited supra; Lerner, *Yale J. Biol. Med.*, cited supra; Kenneth, *Monoclonal Antibodies*, cited supra). Moreover, the ordinary skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines may be used as a fusion partner according to standard techniques, e.g., the P3-NS1/1-Ag4-1, P3-x63-Ag8.653 or Sp2/O-Ag14 myeloma lines. These myeloma lines are available from the American Type Culture Collection (ATCC), Rockville, Md. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind NIP45, e.g., using a standard ELISA assay.

Alternative to preparing monoclonal antibody-secreting hybridomas, a monoclonal anti-NIP45 antibody can be identified and isolated by screening a recombinant combinatorial immunoglobulin library (e.g., an antibody phage display library) with NIP45 to thereby isolate immunoglobulin library members that bind NIP45. Kits for generating and screening phage display libaries are commercially available (e.g., the Pharmacia Recombinant Phage Antibody System, Catalog No. 27-9400-01; and the Stratagene SurfZAP™ Phage Display Kit, Catalog No. 240612). Additionally, examples of methods and reagents particularly amenable for use in generating and screening antibody display library can be found in, for example, Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Bio/Technology* 9:1370–1372; Hay et al. (1992) *Hum Antibod Hybridomas* 3:81–85; Huse et al. (1989) *Science* 246:1275–1281; Griffiths et al. (1993) *EMBO J* 12:725–734; Hawkins et al. (1992) *J Mol Biol* 226:889–896; Clarkson et al. (1991) *Nature* 352:624–628; Gram et al. (1992) *PNAS* 89:3576–3580; Garrad et al. (1991) *Bio/Technology* 9:1373–1377; Hoogenboom et al. (1991) *Nuc Acid Res* 19:4133–4137; Barbas et al. (1991) *PNAS* 88:7978–7982; and McCafferty et al. *Nature* (1990) 348:552–554.

Additionally, recombinant anti-NIP45 antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Patent Publication PCT/US86/02269; Akira, et al. European Patent Application 184,187; Taniguchi, M., European Patent Application 171, 496; Morrison et al. European Patent Application 173,494; Neuberger et al. PCT Application WO 86/01533; Cabilly et al. U.S. Pat. No. 4,816,567; Cabilly et al. European Patent Application 125,023; Better et al. (1988) *Science* 240:1041–1043; Liu et al. (1987) *PNAS* 84:3439–3443; Liu et al. (1987) *J. Immunol.* 139:3521–3526; Sun et al. (1987) *PNAS* 84:214–218; Nishimura et al. (1987) *Canc. Res.* 47:999–1005; Wood et al. (1985) *Nature* 314:446–449; and Shaw et al. (1988) *J. Natl Cancer Inst.* 80:1553–1559); Morrison, S. L. (1985) *Science* 229:1202–1207; Oi et al. (1986) *BioTechniques* 4:214; Winter U.S. Pat. No. 5,225, 539; Jones et al. (1986) *Nature* 321:552–525; Verhoeyan et al. (1988) *Science* 239:1534; and Beidler et al. (1988) *J. Immunol.* 141:4053 –4060.

An anti-NIP45 antibody (e.g., monoclonal antibody) can be used to isolate NIP45 by standard techniques, such as affinity chromatography or immunoprecipitation. An anti-NIP45 antibody can facilitate the purification of natural NIP45 from cells and of recombinantly produced NIP45 expressed in host cells. Moreover, an anti-NIP45 antibody can be used to detect NIP45 protein (e.g., in a cellular lysate or cell supernatant). Detection may be facilitated by coupling (i.e., physically linking) the antibody to a detectable substance. Accordingly, in one embodiment, an anti-NIP45 antibody of the invention is labeled with a detectable substance. Examples of detectable substances include various enzymes, prosthetic groups, fluorescent materials, luminescent materials and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include $^{125}$I, $^{131}$I, $^{35}$S or $^{3}$H.

IV. Pharmaceutical Compositions

The NIP45 proteins and anti-NIP45 antibodies of the invention can be incorporated into pharmaceutical compositions suitable for administration. Such compositions typically comprise the protein or antibody and a pharmaceutically acceptable carrier. As used herein the term "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. For example, solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a NIP45 protein or anti-NIP45 antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These may be prepared according to methods known to those skilled in the art, for example, as described in U.S. Pat. No. 4,522,811.

V. Methods of the Invention

Another aspect of the invention pertains to a method of using the various NIP45 compositions of the invention. For example, the invention provides a method for detecting the presence of NIP45 protein or mRNA in a biological sample. The method involves contacting the biological sample with an agent capable of detecting NIP45 protein or mRNA such that the presence of NIP45 protein or mRNA is detected in the biological sample. A preferred agent for detecting NIP45 mRNA is a labeled nucleic acid probe capable of hybridizing to NIP45 mRNA. The nucleic acid probe can be, for example, the NIP45 cDNA of SEQ ID NO: 1, or a portion thereof, such as an oligonucleotide of at least 15, 30, 50, 100, 200, 300, 400, 500, 600, 700, 800, 900 or 1000 nucleotides in length and sufficient to specifically hybridize under stringent conditions to NIP45 mRNA. A preferred agent for detecting NIP45 protein is a labeled antibody capable of binding to NIP45 protein. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids. For example, techniques for detection of NIP45 mRNA include Northern hybridizations and in situ hybridizations. Techniques for detection of NIP45 protein include enzyme linked immunosorbent assays (ELISAs), Western blots, immunoprecipitations and immunofluorescence.

The invention further provides methods for identifying agents that modulate an interaction between NIP45 and an NF-AT family protein. In one embodiment, the method comprises:

a) combining:

(i) NIP45, or an NF-AT-interacting portion thereof; and (ii) an NF-AT family protein, or a NIP45-interacting portion thereof;

in the presence and absence of a test compound;

b) determining the degree of interaction between (i) and (ii) in the presence and absence of the test compound; and c) identifying an agent that modulates an interaction between NIP45 and an NF-AT family protein.

Isolated NIP45 and/or NF-AT family proteins may be used in the method, or, alternatively, only portions of NIP45 and/or an NF-AT family protein may be used. For example, an isolated NF-AT Rel Homology Domain (or a larger subregion of NF-AT that includes the RHD) can be used as the NIP45-interacting portion of NF-AT. Likewise, a portion of NIP45 capable of binding to the NF-AT RHD may be used. In a preferred embodiment, one or both of (i) and (ii) are fusion proteins, such as GST fusion proteins (e.g., GST-NF-AT RHD can be used as the NIP45-interacting portion of NF-AT). The degree of interaction between (i) and (ii) can be determined, for example, by labeling one of the proteins with a detectable substance (e.g., a radiolabel), isolating the non-labeled protein and quantitating the amount of detectable substance that has become associated with the non-labeled protein. The assay can be used to identify agents that either stimulate or inhibit the interaction between NIP45 and an NF-AT family protein. An agent that stimulates the interaction between NIP45 and an NF-AT family protein is identified based upon its ability to increase the degree of interaction between (i) and (ii) as compared to the degree of interaction in the absence of the agent, whereas an agent that inhibits the interaction between NIP45 and an NF-AT family protein is identified based upon its ability to decrease the degree of interaction between (i) and (ii) as compared to the degree of interaction in the absence of the agent. Assays systems for identifying agents that modulate SH2 domain-ligand interactions as described in U.S. Pat. No. 5,352,660 by Pawson can be adapted to identifying agents that modulate the NIP45/NF-AT RHD interaction.

In another embodiment, the invention provides a method for identifying a compound that modulates the expression or activity of NIP45. The method comprises:

a) preparing an indicator cell, wherein said indicator cell contains:

i) a recombinant expression vector encoding NIP45; and ii) a vector comprising regulatory sequences of a Th2-associated cytokine gene operatively linked a reporter gene;

b) contacting the indicator cell with a test compound;

c) determining the level of expression of the reporter gene in the indicator cell in the presence of the test compound;

d) comparing the level of expression of the reporter gene in the indicator cell in the presence of the test compound with the level of expression of the reporter gene in the indicator cell in the absence of the test compound; and e) identifying a compound that modulates the expression or activity of NIP45.

Recombinant expression vectors that can be used for expression of NIP45 in an indicator cell are known in the art (see discussions above and also the Examples). In one embodiment, within the expression vector the NIP45 coding sequences are operatively linked to regulatory sequences that allow for constitutive expression of NIP45 in the indicator cell (e.g., viral regulatory sequences, such as a cytomegalovirus promoter/enhancer, can be used). Use of a recombinant expression vector that allows for constitutive expression of NIP45 in the indicator cell is preferred for identification of compounds that enhance or inhibit the activity of NIP45. In an alternative embodiment, within the expression vector the NIP45 coding sequences are operatively linked to regulatory sequences of the NIP45 gene (i.e., the promoter regulatory region derived from the endogenous NIP45 gene). Use of a recombinant expression vector in which NIP45 protein expression is controlled by the native regulatory sequences of the NIP45 gene is preferred for identification of compounds that enhance or inhibit the transcriptional expression of NIP45.

Preferably, the Th2-associated cytokine is interleukin-4. It has previously shown that Th2-specific, inducible IL-4 expression can be directed by as little as 157 bp of the proximal IL-4 promoter in Th2 cells (Hodge, M. et al. (1995) *J. Immunol.* 154:6397–6405). Accordingly, in one embodiment, the method utilizes a reporter gene construct containing this region of the proximal IL-4 promoter, most preferably nucleotides −157 to +58 (relative to the start site of transcription at +1) of the IL-4 promoter. Alternatively, stronger reporter gene expression can be achieved using a longer portion of the IL-4 upstream regulatory region, such as about 3 kb of upstream regulatory sequences. Suitable reporter gene constructs are described in Todd, M. et al. (1993) *J. Exp. Med.* 177:1663–1674.

A variety of reporter genes are known in the art and are suitable for use in the screening assays of the invention. Examples of suitable reporter genes include those which encode chloramphenicol acetyltransferase, beta-galactosidase, alkaline phosphatase or luciferase. Standard methods for measuring the activity of these gene products are known in the art.

A variety of cell types are suitable for use as an indicator cell in the screening assay. Preferably a cell line is used which does not normally express NIP45, such as a B cell (e.g., the M12 B lymphoma cell line) or nonlymphoid cell lines, such as the HepG2 hepatoma cell line.

In one embodiment, the level of expression of the reporter gene in the indicator cell in the presence of the test compound is higher than the level of expression of the reporter gene in the indicator cell in the absence of the test compound and the test compound is identified as a compound that stimulates the expression or activity of the transcription factor. In another embodiment, the level of expression of the reporter gene in the indicator cell in the presence of the test compound is lower than the level of expression of the reporter gene in the indicator cell in the absence of the test compound and the test compound is identified as a compound that inhibits the expression or activity of the transcription factor.

In yet another embodiment, the invention provides a method identifying a protein that interacts with NIP45 comprising:
a) providing a two hybrid assay including a host cell that contains:
   i) a reporter gene operably linked to a transcriptional regulatory sequence;
   ii) a first chimeric gene that encodes a first fusion protein, said first fusion protein including NIP45;
   iii) a library of second chimeric genes that encodes second fusion proteins;
   wherein expression of the reporter gene is sensitive to interactions between the first fusion protein, the second fusion protein and the transcriptional regulatory sequence;
b) determining the level of expression of the reporter gene in the host cell; and
c) identifying a protein that interacts with NIP45.

The method of the invention for identifying proteins that interact with NIP45 can be designed based on the two-hybrid assay system (also referred to as an interaction trap assay) known in the art (see e.g., Field U.S. Pat. No. 5,283,173; Zervos et al. (1993) *Cell* 72:223–232; Madura et al. (1993) *J. Biol. Chem.* 268:12046–12054; Bartel et al. (1993) *Biotechniques* 14:920–924; and Iwabuchi et al. (1993) *Oncogene* 8:1693–1696). The two-hybrid assay is generally used for identifying proteins that interact with a particular target protein. The assay employs gene fusions to identify proteins capable of interacting to reconstitute a functional transcriptional activator. The transcriptional activator consists of a DNA-binding domain and a transcriptional activation domain, wherein both domains are required to activate transcription of genes downstream from a target sequence (such as an upstream activator sequence (UAS). for GAL4). DNA sequences encoding a target "bait" protein are fused to either of these domains and a library of DNA sequences is fused to the other domain. "Fish" fusion proteins (generated from the fusion library) capable of binding to the target-fusion protein (e.g., a target GAL4-fusion "bait") will generally bring the two domains (DNA-binding domain and transcriptional activation domain) into close enough proximity to activate the transcription of a reporter gene inserted downstream from the target sequence. Thus, the "fish" proteins can be identified by their ability to reconstitute a functional transcriptional activator (e.g., a functional GAL4 transactivator).

This general two-hybrid system can be applied to the identification of proteins that interact with NIP45 by construction of a target NIP45 fusion protein (e.g., a NIP45/GAL4 binding domain fusion as the "bait") and a cDNA library of "fish" fusion proteins (e.g., a cDNA/GAL4 activation domain library). The cDNA library can be prepared from a cell type of interest to identify proteins in that cell type that interact with NIP45. For example, the cDNA library can be prepared from T cells to identify proteins in T cells that interact with NIP45. The expression vector encoding the NIP45 fusion protein and the cDNA library are then introduced into a host cell that also contains a reporter gene construct linked to a regulatory sequence responsive to NIP45 (e.g., a region of the IL-4 promoter or a promoter containing NF-AT sites). cDNAs encoding proteins that interact with NIP45 can be identified based upon transactivation of the reporter gene construct. For further er description of the two hybrid assay system, see Example 1.

Yet another aspect of the invention pertains to methods of modulating NIP45 activity in a cell. The modulatory methods of the invention involve contacting the cell with an agent that modulates NIP45 activity such that NIP45 activity in the cell is modulated. The agent may act by modulating the activity of NIP45 protein in the cell or by modulating transcription of the NIP45 gene or translation of the NIP45 mRNA. As used herein, the term "modulating" is intended to include inhibiting or decreasing NIP45 activity and stimulating or increasing NIP45 activity. Accordingly, in one embodiment, the agent inhibits NIP45 activity. An inhibitory agent may function, for example, by directly inhibiting NIP45 activity or by inhibiting an interaction between NF-AT and NIP45. In another embodiment, the agent stimulates NIP45 activity. A stimulatory agent may function, for example, by directly stimulating NIP45 activity or by promoting an interaction between NF-AT and NIP45. Methods for modulating NIP45 activity are described further in U.S. Ser. No. 08/755,592, entitled "Methods for Regulating T cell Subsets by Modulating Transcription Factor Activity", filed on Nov. 25, 1996, the entire contents of which are expressly incorporated herein by reference.

This invention is further illustrated by the following examples which should not be construed as limiting. The contents of all references, patents and published patent applications cited throughout this application are hereby incorporated by reference. Nucleotide and amino acid sequences deposited in public databases as referred to herein are also hereby incorporated by reference.

EXAMPLE 1

Isolation of a NIP45 cDNA Using a Yeast Two-Hybrid Interaction Trap Assay

A yeast two-hybrid interaction trap assay was used to isolate proteins that could directly bind to the RHD of NF-ATp. An NF-ATp(RHD)-Gal4 fusion protein was prepared for use as the "bait" in the yeast two-hybrid assay by cloning a 900 bp fragment of murine NF-ATp (McCaffrey, P. G. et al. (1993) *Science* 262:750–754), spanning amino acids 228 to 520, into the BamHI site of vector pEG202 (Gyuris, J. et al. (1993) *Cell* 75:791–803). In frame fusion of the NF-AT(p) polypeptide sequences to the Gal4 sequences was confirmed by DNA sequence analysis. This bait was used to screen a cDNA library prepared from the murine T cell line D10, constructed in the plasmid pJG4-5, to select for clones encoding polypeptides that interacted with the bait, using methodologies known in the art (see Gyuris, J. et al. (1993) *Cell* 75:791–803).

One class of interactors encoding a fusion protein with apparently high affinity for the NF-ATp(RHD)-Gal4 bait, as exhibited by high level of β-galactosidase activity and ability to confer leucine prototrophy, was isolated and termed NIP45 (NF-AT Interacting Protein 45). FIG. 1 shows a photograph of yeast colonies (three representatives for each plasmid combination), cotransformed with the NIP45 plasmid and either the NF-ATp-RHD bait or control baits (Max-Gal4, CDK2-Gal4 and the control vector pEG202, expressing only an epitope tagged Gal4 protein), together with the LacZ reporter plasmid pSH18. The yeast colonies had been selected on appropriate media and were spotted onto plates containing Xgal and the nonrepressing carbon source galactose. Yeast colonies cotransformed with the NIP45 plasmid and the NF-ATp-RHD bait were blue in color, demonstrating expression of the LacZ reporter plasmid (indicative of NIP-45/NF-ATp-RHD interaction), whereas yeast colonies transformed with the NIP45 plasmid and the control baits were white in color, indicating no interaction of NIP45 with the control baits. Transformants were also tested on galactose containing media lacking leucine, and only those containing the NIP45 plasmid and the NF-ATp-RHD bait grew, further indicating the specific interaction of NIP45 with NF-ATp-RHD. The NIP45 cDNA isolated by the two-hybrid assay was a 1.9 kb DNA fragment.

EXAMPLE 2

Interaction of NIP45 and NF-ATp in vivo in Mammalian Cells

The ability of the NIP45 polypeptide to interact specifically with NF-ATp in vivo was tested in mammalian cells. The 1.9 kb NIP45 cDNA insert selected in the yeast two-hybrid system (described in Example 1) was subcloned into a mammalian expression vector which fuses the coding region to an epitope tag from a influenza hemagglutinin (HA) peptide, vector pCEP4-HA (Herrscher, R. F. et al. (1995) *Genes Dev.* 9:3067–3082), to create the expression vector NIP45-HA. This tagged construct was then cotransfected with an NF-ATp expression plasmid into HepG2 cells (which express low levels of NF-ATp). As controls, HepG2 cells also were cotransfected with NIP45-HA along with the parental expression vector for the NF-ATp construct (i.e., the expression vector without the NF-ATp insert) or with the NF-ATp expression vector along with an out of frame fusion of NIP45 with the epitope tag. Lysates were prepared from the transfected cells and immunoprecipitated with anti-NF-ATp antibody. Western blot analysis was then performed on the immunoprecipitated material using either anti-NF-ATp or anti-HA antibodies.

Figure 2:
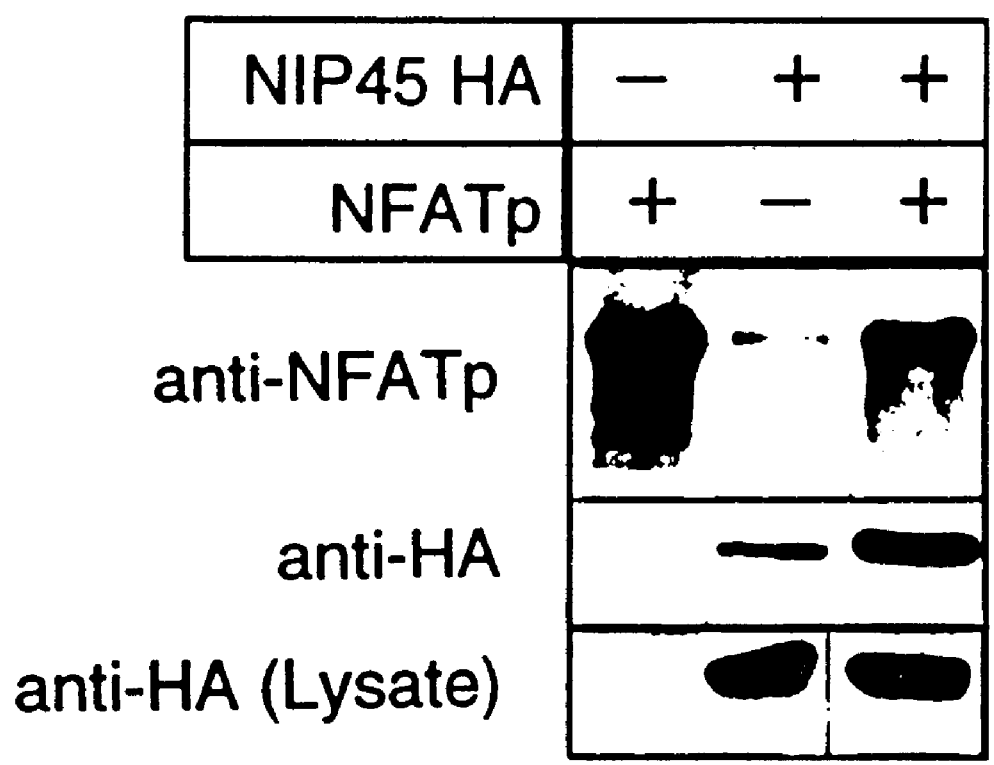
FIG. 2 is a photograph of an immunoprecipitation/Western blot experiment demonstrating that NIP45 and NF-ATp interact in HepG2 cells.

The results of this experiment are shown in FIG. 2. Western blot analysis of these samples using an HA-specific monoclonal antibody (mAb) demonstrated that the anti-NF-ATp antibody used for immunoprecipitation coimmunoprecipitated the HA-tagged NIP45 polypeptide. The lane showing transfection with only NIP45-HA (middle lane) reveals the low endogenous level of NF-ATp present in these cells. The amount of HA-tagged NIP45 protein immunoprecipitated was further increased by cotransfection with the NF-ATp expression plasmid demonstrating the specificity of this interaction (right lane). Western blot analysis of untreated lysates demonstrated that equivalent levels of NIP45-HA polypeptide were expressed in the samples tested for coimmunoprecipitation of NIP45-HA anti-NF-ATp antibodies. Furthermore, no immunoreactive material for either NF-ATp or the HA tagged protein was detected when performing immunoprecipitation using normal rabbit serum. These experiments demonstrate that NF-AT and NIP45 physically associate in vivo in mammalian cells.

EXAMPLE 3

Structural Analysis of NIP45 cDNAs

Figure 3:
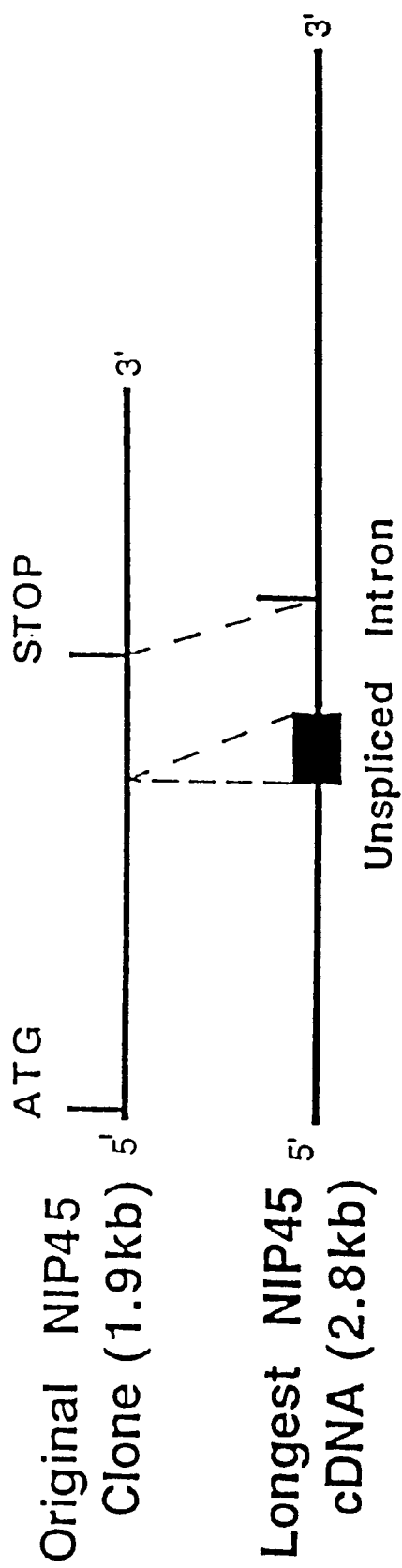
FIG. 3 is a schematic diagram comparing the structures of the original NIP45 cDNA clone isolated from the yeast two-hybrid screen (top) and the longest NIP45 cDNA clone isolated from a D10.G4 lambda zap II library (bottom).

The 1.9 kb NIP45 cDNA insert from the clone isolated using the two-hybrid assay (described in Example 1) was used to screen a D10.G4 T cell lambda zap II cDNA library (Stratagene) to identify full length clones. Screening of a library containing approximately $8 \times 10^5$ clones yielded 7 hybridizing clones most of which did not extend as far towards the 5' end as the original isolate. Sequence analysis of the longest clone (2.8 kb), however, demonstrated identity to the original clone at the 5' end. The structures of the original 1.9 kb cDNA isolate and the longest 2.8 kb cDNA isolate are compared in FIG. 3. The 2.8 kb cDNA isolate contained an additional segment of 180 bp located 868 bp downstream from the 5' end of the original clone. Junction sequences at the ends of this 180 nucleotide segment indicate it to be an unspliced intron and conceptual translation of the nucleotide sequence within this region revealed an in-frame stop codon. Much of the additional sequence in this clone was at the 3' end and represented an extensive 3' untranslated region followed by a poly-A+ tail (see FIG. 3). Such extensive 3' untranslated regions have been observed in many genes. Allowing for the splicing of the small intron and translation of the single large open reading frame, the 2.8 kb cDNA clone is predicted to encode an identical polypeptide to that of the original 1.9 kb isolate.

The nucleotide and predicted amino acid sequences of the 1.9 kb cDNA isolate are shown in FIG. 4 (and in SEQ ID NOs: 1 and 2, respectively). The coding region is shown from the first initiation codon through the first in frame stop codon. The nucleotide and amino acid positions are indicated to the right of the primary sequence. Conceptual translation of the 1.9 kb nucleotide sequence predicted a polypeptide of 412 amino acids with a molecular mass of 45 Kd, and hence the protein has been termed NF-AT Interacting Protein 45 (NIP45). Inspection of the amino acid sequence of NIP45 revealed a highly basic domain at the N-terminus, in which 13 of 32 amino acid are basic. This region is underlined in FIG. 4. This basic region appears as a hydrophilic stretch in the hydrophobicity plot shown in FIG. 5.

EXAMPLE 4

Tissue Expression of NIP45 mRNA

Figure 6:
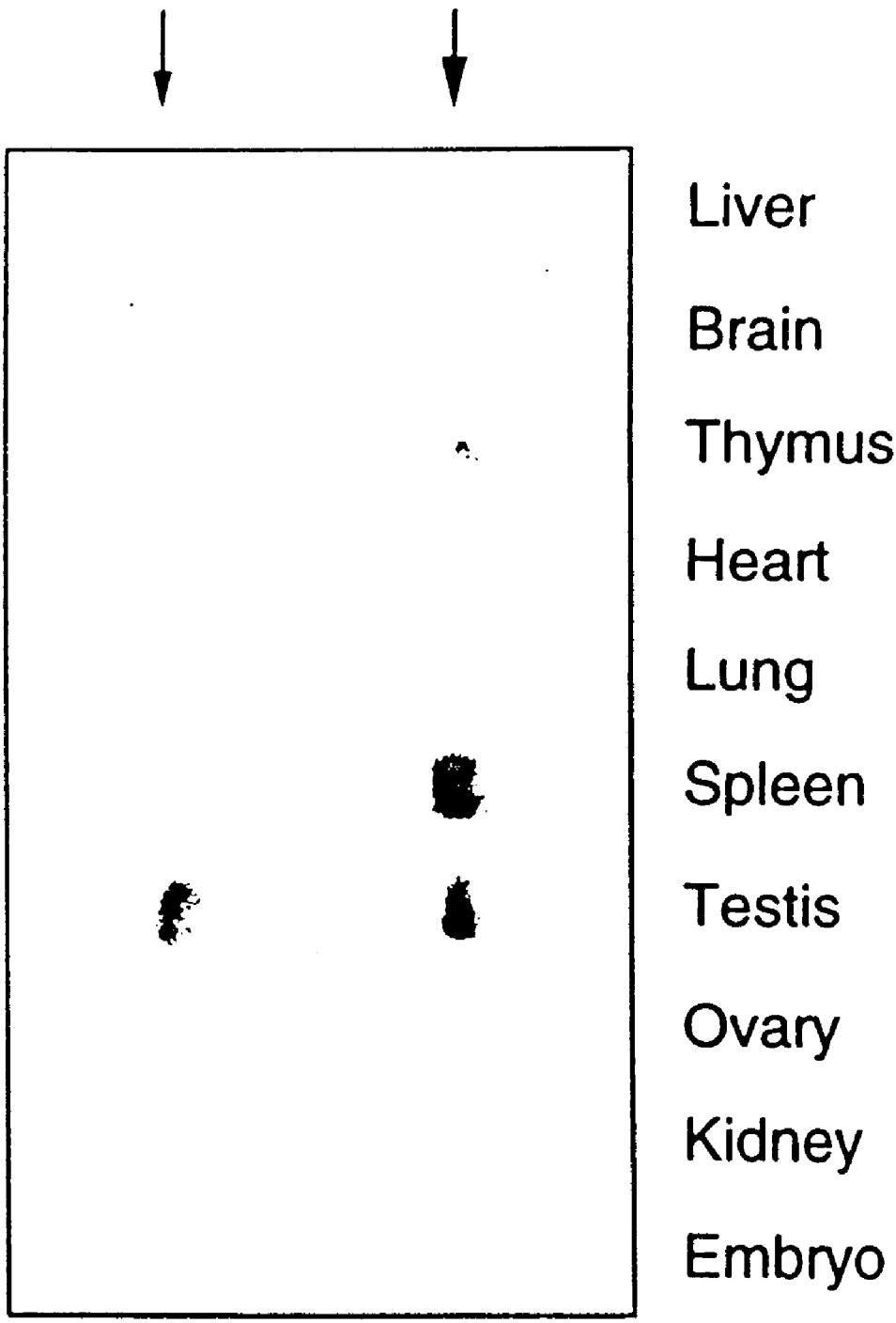
FIG. 6 is a photograph of an RNA blot analysis of NIP45 transcript levels in various tissues.

Northern blot analysis of RNA from different murine tissues was performed to investigate the tissue expression of NIP45 mRNA. 10 μg of total RNA from various tissues was separated on denaturing agarose gels, blotted and hybridized with a radiolabelled 1.4 kb NIP45 cDNA fragment. Samples were controlled for equivalent loading of RNA by comparison of ethidium bromide fluorescence. The results of the Northern blot analysis are shown in FIG. 6. The hybridizations revealed a transcript of approximately 3.1 kb, which is of comparable size to the longest cDNA clones. RNA from testis contained an additional 1.4 Kb hybridizing species. The highest levels of NIP45 transcripts were seen in spleen, thymus and testis. The preferential expression in lymphoid organs may indicate a specific function for NIP45 in the immune system. The low intensity hybridization signal and the rare occurrence of NIP45 cDNA clones in the T cell cDNA library indicate that the NIP45 RNA is a relatively rare message.

EXAMPLE 5

Subcellular Localization of NIP45

Figure 7C:
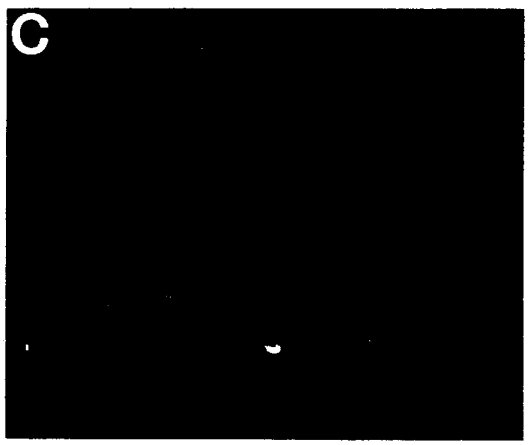
FIG. 7C is a photograph of immunofluorescence analysis of unstimulated BHK cells transfected with an expression construct encoding NF-AT4 and probed with an anti-NF-AT4 specific antibody as the primary antibody and an indocarbocyanine labelled goat anti-mouse secondary reagent.
Figure 7D:
FIG. 7D is a photograph of the same cells depicted in FIG. 7C counterstained with the DNA staining dye Hoechst 33258.

Subcellular localization of epitope tagged NIP45 protein was determined by indirect immunofluorescence. BHK cells were transfected with 1 μg of an expression construct encoding an HA-epitope tagged NIP45 (pCEP4-HA), using methodologies known in the art (see Heald, R. et al. (1993) *Cell* 74:463–474). Transfected cells were incubated overnight, fixed, permeabilized as described (Heald, R. et al. (1993) supra) and probed with an anti-HA mAb 12CA5 (Boehringer Mannheim) plus indocarbocyanine labelled donkey anti-mouse antibody (Jackson ImmunoResearch) and then counterstained with the dye Hoechst 33258. The results are shown in FIGS. 7A–B. Nuclear staining of NIP45 was observed with the indocarbocyanine labelled secondary reagent (see FIG. 7A) by comparison to the same cells counterstained with the DNA staining dye Hoechst 33258 (see FIG. 7B). The fluorescence pattern indicates that NIP45 is evenly distributed throughout the nucleus. Furthermore, this pattern matched that seen for cells transfected with NF-AT4 and stimulated with ionomycin (Shibasaki, F. et al. (1996) *Nature* 382:370–373; see also below). Stimulation with PMA and/or ionomycin did not affect the subcellular localization of this NIP45.

Figure 7E:
FIG. 7E is a photograph of immunofluorescence analysis of ionomycin-treated BHK cells transfected with an expression construct encoding NF-AT4 and probed with an anti-NF-AT4 specific antibody as the primary antibody and an indocarbocyanine labelled goat anti-mouse secondary reagent.
Figure 7F:
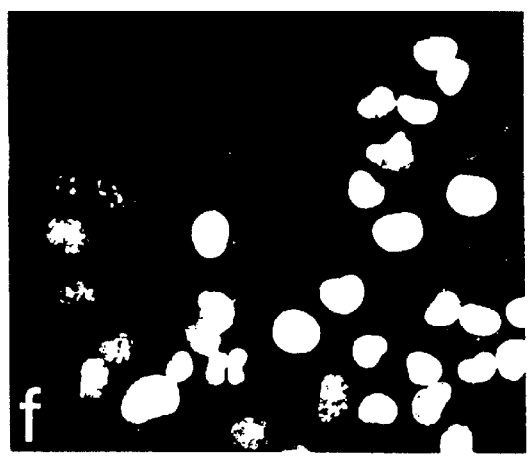
FIG. 7F is a photograph of the same cells depicted in FIG. 7D counterstained with the DNA staining dye Hoechst 33258.

Control experiments were also performed on BHK cells transfected with NF-AT4. Cells were incubated overnight in culture media and either fixed directly or first stimulated with 1 mM ionomycin for 10 minutes before fixation and then processed as described above. The results are shown in FIGS. 7C–F. Unstimulated (FIGS. 7C and 7D) or ionomycin treated (FIGS. 7E and 7F) NF-AT4 transfectants were probed with an anti-NF-AT4 specific antibody followed by a indocarbocyanine labelled secondary reagent and Hoechst 33258. Indocarbocyanine fluorescence demonstrates the pattern of staining for cytoplasmic localized NF-AT4 in unstimulated transfectants (FIG. 7C) and nuclear localized NF-AT4 in stimulated cells (FIG. 7E). Adjacent panels (FIG. 7D and 7F, respectively) show the same field exposed for detection of nuclei by staining with Hoechst 33258.

The effect of NIP45 on the nuclear translocation of NF-AT4 also was investigated. HepG2 cells were transfected with either NF-AT4 or NF-AT4 plus NIP45 and stimulated the following day with 1 μM ionomycin for 0, 2, 4, 8 or 15 minutes. For one sample, the cells were stimulated for 15 minutes with ionomycin and then washed with fresh media and allowed to rest for an additional 15 minutes (indicated as "15 min.+15 min. rest" in Table 1). This analysis is designed to examine the function of NIP45 as a nuclear retention factor. Fifteen minutes has been shown to be sufficient time for NF-AT4 to be exported to the cytoplasm (Shibasaki, F. et al. (1996) *Nature* 382:370–373). All samples were then fixed and analyzed by immunoflourescence for translocation of NF-AT4 as described above. The results are summarized below in Table 1. Subcellular localization of NF-AT4 in the cytoplasm is indicated by a (−) and nuclear translocation of NF-AT4 is indicated by (+).

TABLE 1

Nuclear Translocation of NF-AT4

| Time | Ionomycin | Ionomycin + NIP45 |
| --- | --- | --- |
| 0 min. | − | − |
| 2 min. | +/− | +/− |
| 4 min. | +/− | +/− |
| 8 min. | + | + |
| 15 min. | + | + |
| 15 min. + 15 min. rest | − | − |

No difference in the rate of nuclear import or export of NF-AT4 was observed in the presence of NIP45, indicating that nuclear trafficking of NF-AT4 in response to changes in intracellular calcium levels was not affected by the overexpression of exogenous NIP45.

EXAMPLE 6

Functional Activity of NIP45 in Regulating Gene Expression

Figure 8:
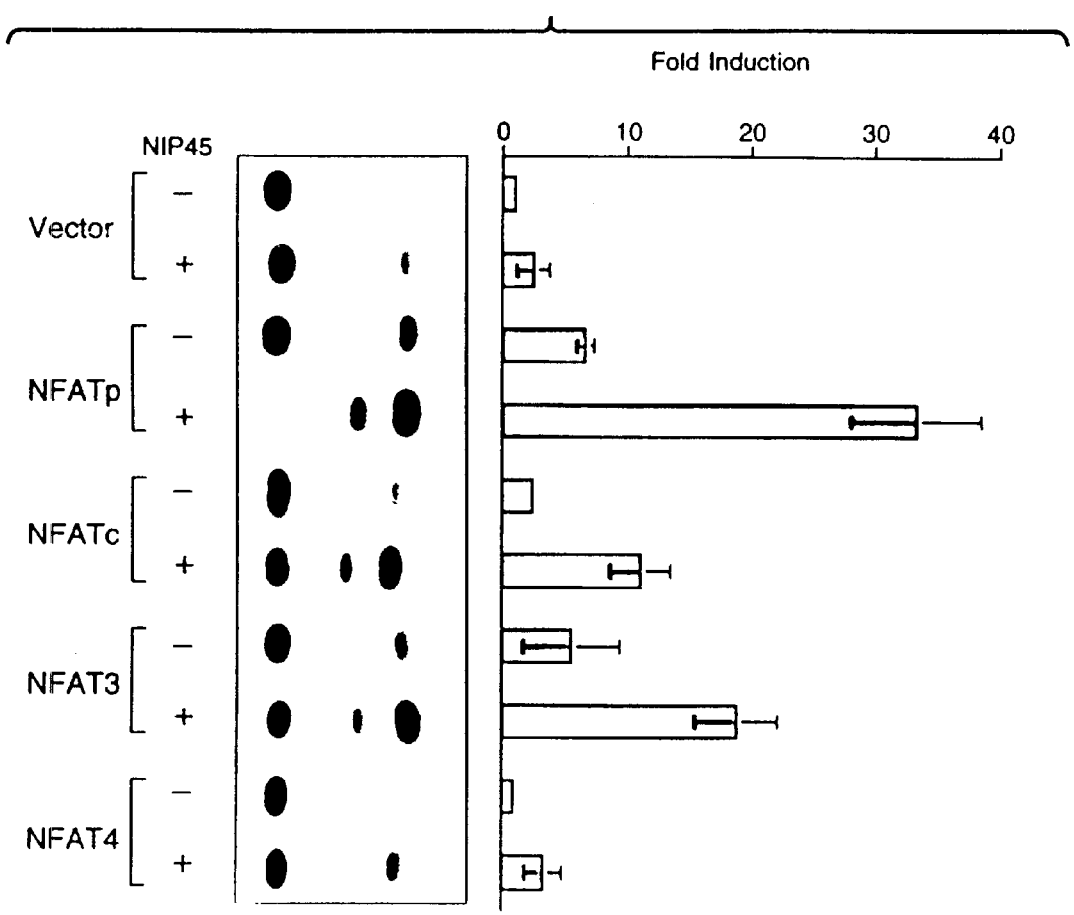
FIG. 8 is a photograph of CAT assay results (left) and a bar graph quantitating the relative fold induction of CAT activity (right) in HepG2 cells transfected with a 3× NF-AT-CAT reporter gene construct (containing three NF-AT binding sites) and either a control expression plasmid or an NF-AT family expression plasmid (NF-ATp, NF-ATc, NF-AT3 or NF-AT4), alone (−) or in combination with a NIP45 expression plasmid (+).

To test for a functional role of NIP45 in NF-AT-driven transcription, NIP45 was expressed at high levels in HepG2 cells. HepG2 cells were chosen because they have low levels of endegenous NF-AT, and ectopic expression of NF-AT family member proteins has been shown to transactivate NF-AT-driven transcription in this cell line in the absence of exogenous stimulation (Hoey, T. et al. (1995) *Immunity* 2:461–472). HepG2 cells were transfected with a 3× NF-AT-CAT reporter from the IL-2 gene (Venkataraman, L. et al. (1994) *Immunity* 1:189–196) and control or expression plasmids for a NIP45 and NF-AT family members (NF-ATp, NF-ATc, NF-AT3, NF-AT4). HepG2 cells were transfected by the DEAE-Dextran method as described in Hoey, T. et al. (1995) supra, and CAT assays were performed according to standard methodologies. The results are shown in FIG. 8. One representative assay for each combination is shown adjacent to a bar graph representing relative CAT activity for each group. Fold induction was calculated by normalizing the CAT activity of cells transfected with the CAT reporter and each parental expression vector to one. Values represent the relative level of CAT expression above this control transfection. All transfections were performed at least three times with one representative autoradiograph shown.

Transfection of NIP45 alone into HepG2 cells with a 3× NF-AT-CAT reporter did not lead to a significant increase in CAT expression demonstrating that NIP45 cannot act on its own to transactivate an NF-AT target sequence. Overexpression of NF-ATp alone resulted in substantial (6-fold over vector control) transactivation of the NF-AT-CAT reporter, consistent with previous reports (Hoey, T. et al. (1995) supra). Cotransfection of NIP45 plus NF-ATp resulted in a 4–5 fold increase in CAT activity relative to transfection with NF-ATp alone and a 25–30 fold increase over that seen with vector alone. This increase was not observed when a mutant 3× NF-AT-CAT reporter or a control MHC class II promoter reporter was used thus demonstrating its target site specificity. To confirm that the polypeptide product encoded by the NIP45 cDNA was responsible for this enhanced transactivation, a frame shift mutation was introduced in the coding region by creating a two base deletion at nucleotide 50. This alteration results in the introduction of missense mutations at amino acid 13 and termination of the polypeptide after an additional 22 residues. Assays using this NIP45Δ construct demonstrated its failure to transactivate the NF-AT reporter in the presence or absence of NF-ATp thus confirming that the enhanced transactivation observed was due to the polypeptide expressed from NIP45 cDNA. Transactivation experiments were also performed in the B cell line M12 and the T cell clone D10 with similar although less dramatic results, which may be due to higher levels of endogenous NIP45 or NF-ATp in these latter cell lines. These experiments demonstrate that NIP45 substantially and specifically potentiates transcription induced by NF-ATp, an activity that requires interaction with NF-ATp.

NF-AT proteins share approximately 70% identity within the RHD, raising the possibility that NIP45 could also interact with other NF-AT family members. To test this, NIP45 was cotransfected as above with expression constructs encoding either NF-ATc, NF-AT3 or NF-AT4 plus the 3× NF-AT-CAT reporter plasmid. The results of these experiments are also shown in FIG. 8. It has previously been demonstrated that all NF-AT family members can transactivate a reporter gene containing 3 copies of an NF-AT/AP1 site when overexpressed in HepG2 cells, although to different levels (Hoey, T. et al. (1995) supra). In the absence of NIP45, NF-ATp was the most potent transactivator of the NF-AT-CAT reporter followed by NF-ATc and NF-AT3 with only weak transactivation by NF-AT4, consistent with previous data (McCaffrey, P. G. et al. (1993) *Science* 262:750–754). When NF-ATc, NF-AT3 or NF-AT4 were cotransfected with NIP45, NIP45 substantially potentiated both NF-ATc and NF-AT3-driven transactivation and weakly potentiated NF-AT4-mediated transactivation (FIG. 8). Cooperation with NF-ATc in HepG2 cells is consistent with the observation that NIP45 interacts with an NF-ATc RHD bait in yeast cells. Overall, NIP45 overexpression resulted in a 4-fold increase in transactivation by NF-ATc, a 3-fold increase in NF-AT3-driven transactivation and a 2-fold increase in NF-AT4-driven transcription. The ability of NIP45 to potentiate the activity of all NF-AT family members is not surprising given the high degree of sequence conservation of the RHD of the NF-AT family members. A sequence comparison of the NF-AT RHD domains reveals a higher level of sequence identity in the amino terminal portion compared to that of the carboxyl terminus (Hoey, T. et al. (1995) supra). Thus it is likely that the NIP45/NF-AT interaction site is located in the 5' portion of the RHD.

Figure 9:
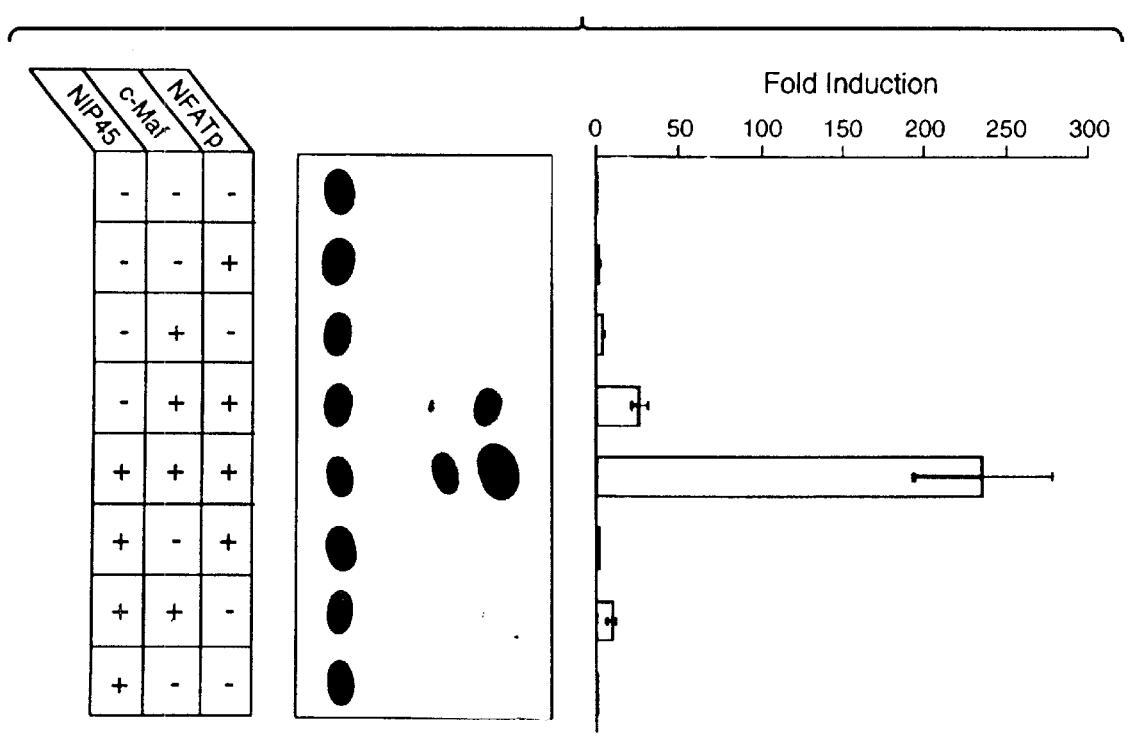
FIG. 9 is a photograph of CAT assay results (left) and a bar graph quantitating the relative fold induction of CAT activity (right) in HepG2 cells transfected with an IL-4-CAT reporter gene construct (extending to −732 bp of the IL-4 promoter) and combinations of NF-ATp, NIP45 and/or c-Maf expression constructs, as indicated.

Although a reporter construct containing multiple copies of the NF-AT binding site provides a sensitive method for measuring transactivation by NF-AT and NIP45, we sought to determine if NIP45 was functional in the context of a native NF-AT-dependent promoter. IL-4 expression is highly tissue specific and restricted to the Th2 subset of T cells and to mast cells. The IL-4 promoter contains multiple NF-AT binding sites which have been shown to be critical for expression of IL-4 (Rooney, J. W. et al. (1995) *Immunity* 2:473–483). Furthermore, the proto-oncogene c-maf has been shown to direct tissue specific expression of IL-4 (U.S. Ser. No. 08/636,602). Thus, the IL-4 promoter is not active in the HepG2 cell line but can be activated by the introduction of NF-ATp and c-maf. In cotransfection experiments carried out as described above, HepG2 cells were transfected with an IL-4-CAT reporter construct (extending to –732 bp of the IL-4 promoter) and expression vectors or controls for NIP45, NF-ATp and c-Maf. The controls for NIP45 was a frame shift mutant at amino acid 13. Controls for NF-ATp and c-Maf 10 were the empty expression vectors pREP4 and pMEX respectively (Ho, I. C. et al. (1996) *Cell* 85:973–983). The results of these experiments are shown in FIG. 9 (representative CAT assays and bar graphs are depicted as in FIG. 8). The data indicate that introduction of NIP45 together with NF-ATp and c-Maf results in an additional 9-fold increase in the activity of the IL-4 promoter relative to that seen for NF-ATp and c-Maf alone. NIP45 also increased the activity of the IL-4 promoter in the absence of transfected NF-ATp, an effect likely due to interaction with endogenous NF-ATp.

EXAMPLE 7

Figure 10:
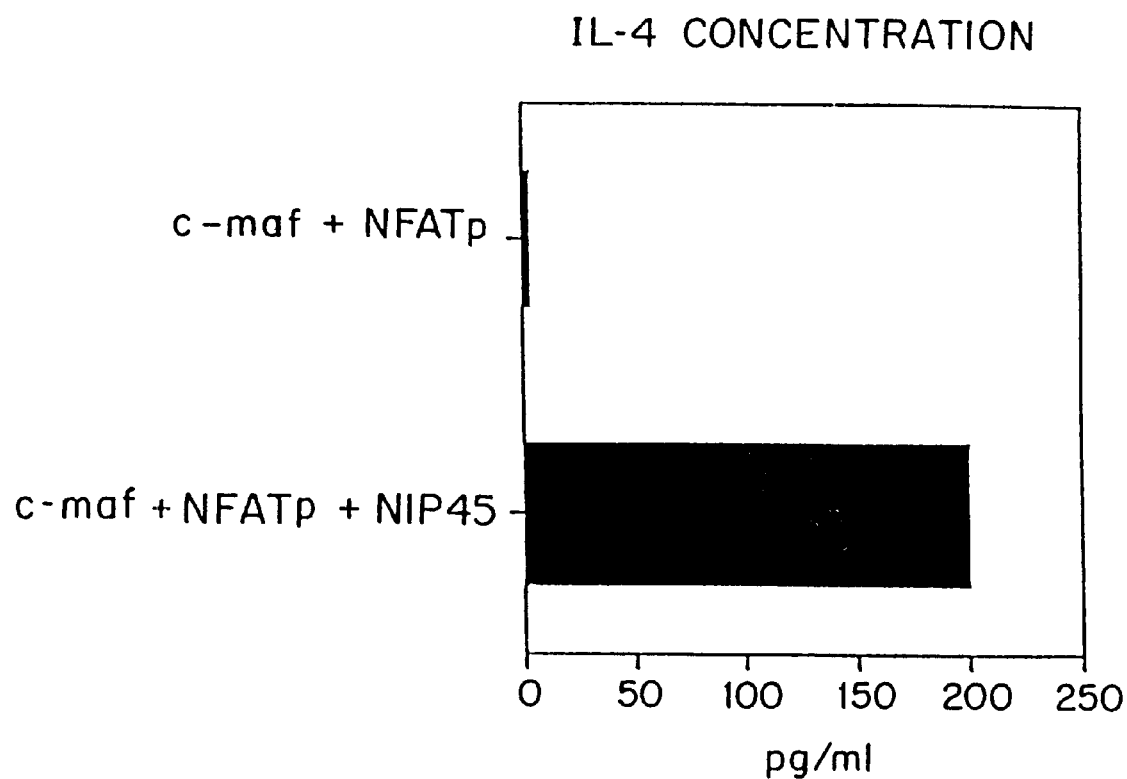
FIG. 10 is a bar graph depicting the level of IL-4 (in pg/ml) in the supernatants of M12 B lymphoma cells transiently cotransfected with expression plasmids for NF-ATp, c-Maf and a pCI vector control (top bar) or expression plasmids for NF-ATp, c-Maf and NIP45 (bottom bar).

Transient Overexpression of NIP45 with NF-ATp and c-Maf Results in Endogenous IL-4 Production To determine whether the combination of NIP45, NF-ATp and c-Maf was sufficient to induce endogenous IL-4 expression by cells that do not normally produce IL-4, M12 B lymphoma cells were transiently cotransfected with expression plasmids for NF-ATp and c-Maf together with NIP45 or pCI vector control. M12 cells were transiently transfected by electroporation as previously described (Ho, I. C. et al. (1996) *Cell* 85:973–983) by incubating $3 \times 10^6$ cells in 0.4 ml of PBS with 5 µg of each plasmid for 10 minutes at room temperature prior to electroporation at 975 µF, 280 V. Levels of IL-4 in the supernatants harvested 72 hours later were measured by a commercially available IL-4 ELISA (Pharmingen), performed according to the manufacturer's instructions except with modification as described (Ho, I. C. et al. (1996) supra). Four independent sets of transient transfections were done and assayed for secretion of IL-4 into the culture supernatant. Results from a representative experiment from one of the four independent transfections is shown in FIG. 10. For each set of transfections, inclusion of NIP45 led to a dramatic increase in IL-4 production. Cells transfected with NIP45 produced 50–200 fold more endogenous IL-4 than cells that did not receive NIP45, in which IL-4 production was near the limit of detection.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. An antibody that specifically binds to a protein comprising the amino acid sequence set forth in SEQ ID NO:2.

2. The antibody of claim 1, which is a monoclonal antibody.

3. An antibody coupled to a detectable substance, wherein the antibody specifically binds to a protein comprising the amino acid sequence set forth in SEQ ID NO:2.

\* \* \* \* \*

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
      (A) LENGTH: 1946 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 13..1248

(xi) SEQUENCE DESCRIPTION: SEQ ID NO: 1:

```
ACAGTGTGGG AG ATG GCG GAA CCA CTG AGG GGA CGT GGT CCG AGG TCC         48
              Met Ala Glu Pro Leu Arg Gly Arg Gly Pro Arg Ser
                1               5                  10

CGC GGT GGC CGA GGC GCT CGG AGA GCC CGA GGC GCC CGT GGC CGG TGT        96
Arg Gly Gly Arg Gly Ala Arg Arg Ala Arg Gly Ala Arg Gly Arg Cys
            15                  20                  25

CCT CGC GCC CGG CAG TCT CCG GCT AGG CTC ATT CCA GAC ACC GTG CTT       144
Pro Arg Ala Arg Gln Ser Pro Ala Arg Leu Ile Pro Asp Thr Val Leu
        30                  35                  40

GTG GAC TTG GTC AGT GAC AGC GAC GAA GAG GTC TTG GAA GTC GCA GAC       192
Val Asp Leu Val Ser Asp Ser Asp Glu Glu Val Leu Glu Val Ala Asp
    45                  50                  55                  60

CCA GTA GAG GTG CCG GTC GCC CGC CTC CCC GCG CCG GCT AAA CCT GAG       240
Pro Val Glu Val Pro Val Ala Arg Leu Pro Ala Pro Ala Lys Pro Glu
                65                  70                  75

CAG GAC AGC GAC AGT GAC AGT GAA GGG GCG GCC GAG GGG CCT GCG GGA       288
Gln Asp Ser Asp Ser Asp Ser Glu Gly Ala Ala Glu Gly Pro Ala Gly
            80                  85                  90

GCC CCG CGT ACA TTG GTG CGA CGG CGG CGG CGG CGG CTG CTG GAT CCC       336
Ala Pro Arg Thr Leu Val Arg Arg Arg Arg Arg Arg Leu Leu Asp Pro
        95                  100                 105

GGA GAG GCG CCG GTG GTC CCA GTG TAC TCC GGG AAG GTA CAG AGC AGC       384
Gly Glu Ala Pro Val Val Pro Val Tyr Ser Gly Lys Val Gln Ser Ser
    110                 115                 120

CTC AAC CTC ATT CCA GAT AAT TCA TCC CTC TTG AAA CTG TGC CCT TCA       432
Leu Asn Leu Ile Pro Asp Asn Ser Ser Leu Leu Lys Leu Cys Pro Ser
125                 130                 135                 140

GAG CCT GAA GAT GAG GCA GAT CTG ACA AAT TCT GGC AGT TCT CCC TCT       480
Glu Pro Glu Asp Glu Ala Asp Leu Thr Asn Ser Gly Ser Ser Pro Ser
                145                 150                 155

GAG GAT GAT GCC CTG CCT TCA GGT TCT CCC TGG AGA AAG AAG CTC AGA       528
Glu Asp Asp Ala Leu Pro Ser Gly Ser Pro Trp Arg Lys Lys Leu Arg
            160                 165                 170

AAG AAG TGT GAG AAA GAA GAA AAG AAA ATG GAA GAG TTT CCG GAC CAG       576
Lys Lys Cys Glu Lys Glu Glu Lys Lys Met Glu Glu Phe Pro Asp Gln
        175                 180                 185

GAC ATC TCT CCT TTG CCC CAA CCT TCG TCA AGG AAC AAA AGC AGA AAG       624
Asp Ile Ser Pro Leu Pro Gln Pro Ser Ser Arg Asn Lys Ser Arg Lys
    190                 195                 200

CAT ACG GAG GCG CTC CAG AAG CTA AGG GAA GTG AAC AAG CGT CTC CAA       672
His Thr Glu Ala Leu Gln Lys Leu Arg Glu Val Asn Lys Arg Leu Gln
205                 210                 215                 220

GAT CTC CGC TCC TGC CTG AGC CCC AAG CAG CAC CAG AGT CCA GCC CTT       720
Asp Leu Arg Ser Cys Leu Ser Pro Lys Gln His Gln Ser Pro Ala Leu
                225                 230                 235

CAG AGC ACA GAT GAT GAG GTG GTC CTA GTG GAA GGG CCT GTC TTG CCA       768
Gln Ser Thr Asp Asp Glu Val Val Leu Val Glu Gly Pro Val Leu Pro
            240                 245                 250

CAG AGC TCT CGA CTC TTT ACA CTC AAG ATC CGG TGC CGG GCT GAC CTA       816
Gln Ser Ser Arg Leu Phe Thr Leu Lys Ile Arg Cys Arg Ala Asp Leu
        255                 260                 265

GTG AGA CTG CCT GTC AGG ATG TCG GAG CCC CTT CAG AAT GTG GTG GAT       864
Val Arg Leu Pro Val Arg Met Ser Glu Pro Leu Gln Asn Val Val Asp
    270                 275                 280

CAC ATG GCC AAT CAT CTT GGG GTG TCT CCA AAC AGG ATT CTT TTG CTT       912
His Met Ala Asn His Leu Gly Val Ser Pro Asn Arg Ile Leu Leu Leu
285                 290                 295                 300
```

```
TTT GGA GAG AGT GAA CTG TCT CCT ACT GCC ACC CCT AGT ACC CTA AAG       960
Phe Gly Glu Ser Glu Leu Ser Pro Thr Ala Thr Pro Ser Thr Leu Lys
                305                 310                 315

CTT GGA GTG GCT GAC ATC ATT GAT TGT GTG GTG CTA GCA AGC TCT TCA      1008
Leu Gly Val Ala Asp Ile Ile Asp Cys Val Val Leu Ala Ser Ser Ser
            320                 325                 330

GAG GCC ACA GAG ACA TCC CAG GAG CTC CGG CTC CGG GTG CAG GGG AAG      1056
Glu Ala Thr Glu Thr Ser Gln Glu Leu Arg Leu Arg Val Gln Gly Lys
        335                 340                 345

GAG AAA CAC CAG ATG TTG GAG ATC TCA CTG TCT CCT GAT TCT CCT CTT      1104
Glu Lys His Gln Met Leu Glu Ile Ser Leu Ser Pro Asp Ser Pro Leu
    350                 355                 360

AAG GTT CTC ATG TCA CAC TAT GAG GAA GCC ATG GGA CTC TCT GGA CAC      1152
Lys Val Leu Met Ser His Tyr Glu Glu Ala Met Gly Leu Ser Gly His
365                 370                 375                 380

AAG CTC TCC TTC TTC TTT GAT GGG ACA AAG CTT TCA GGC AAG GAG CTG      1200
Lys Leu Ser Phe Phe Phe Asp Gly Thr Lys Leu Ser Gly Lys Glu Leu
                385                 390                 395

CCA GCT GAT CTG GGC CTG GAA TCC GGA GAT CTC ATC GAA GTC TGG GGC      1248
Pro Ala Asp Leu Gly Leu Glu Ser Gly Asp Leu Ile Glu Val Trp Gly
            400                 405                 410

TGAAGCTCTC ACCCTGTTCG ACGCAAAGC CAAGACATGG AGACAATAGC TCCCAATTTT    1308

ATTATTGTGA TTTTTCGCCC CATAAGGGCT AACAGAAACT GAATTAGAAC TTGTTTACTT   1368

ATTTATTTCT GGTGCTGGGG ATTGAACCCC AGACTATGCA CATGCTAAGG ATGTATGAAG   1428

TGGAGGCAAA ACCAAGGCAT TACCTTTAGC CAGCCTCTAG TAGACTGTAG TGTCAAGCAA   1488

GTGGCTACTT GGTAGTTGTG TGGCTCTGTG TATGTTTGTG CTGTATTTGG CAGCCCCTGG   1548

GGCACATAGA AGGGACCTTG GCTTCCCTAC CATTTCACGT TCGCTGGTGC CCTTTCCTTC   1608

ATCAGATGAC TTCTGTGAAG CTGCCTATGT TGAGTGTGTT GAACTAAATG AGCTCTGCTT   1668

TGGGTGTCCA GGCCTGGGGT TTGTGCCGCA GTTGGAGCCA GCAGTGACTT CACTCTGACT   1728

TGGGACTGAG AATGCATTTC CTGGTGGAGA CACTCGGGTG CAGAAATATA ACAGAAGGTG   1788

ACATACATGC TGAAGCTGAG GACTAGGTCG AAAGTTAACG ACGTTGCATT TTCAGCCTTG   1848

GGTATCCTCT CTGCCTGCCA GGACTCTAGC CAGTGTCTGG TACACACTTC TTGGCATGGA   1908

CACCTAGGTC GACGCGGGCG CGATTCGGCC GACTCGAG                           1946

(2) INFORMATION FOR SEQ ID NO: 2:

(i) SEQUENCE CHARACTERISTICS:
        (A) LENGTH: 412 amino acids
        (B) TYPE: amino acid
        (D) TOPOLOGY: linear (ii) MOLECULE TYPE: protein (xi) SEQUENCE DESCRIPTION: SEQ ID NO: 2:

Met Ala Glu Pro Leu Arg Gly Arg Gly Pro Arg Ser Arg Gly Gly Arg
 1               5                  10                  15

Gly Ala Arg Arg Ala Arg Gly Ala Arg Gly Arg Cys Pro Arg Ala Arg
            20                  25                  30

Gln Ser Pro Ala Arg Leu Ile Pro Asp Thr Val Leu Val Asp Leu Val
        35                  40                  45

Ser Asp Ser Asp Glu Glu Val Leu Glu Val Ala Asp Pro Val Glu Val
    50                  55                  60

Pro Val Ala Arg Leu Pro Ala Pro Ala Lys Pro Glu Gln Asp Ser Asp
65                  70                  75                  80
```

```
                        -continued

Ser Asp Ser Glu Gly Ala Ala Glu Gly Pro Ala Gly Ala Pro Arg Thr
                85                  90                  95

Leu Val Arg Arg Arg Arg Arg Leu Leu Asp Pro Gly Glu Ala Pro
            100                 105                 110

Val Val Pro Val Tyr Ser Gly Lys Val Gln Ser Ser Leu Asn Leu Ile
            115                 120                 125

Pro Asp Asn Ser Ser Leu Leu Lys Leu Cys Pro Ser Glu Pro Glu Asp
        130                 135                 140

Glu Ala Asp Leu Thr Asn Ser Gly Ser Ser Pro Ser Glu Asp Asp Ala
145                 150                 155                 160

Leu Pro Ser Gly Ser Pro Trp Arg Lys Lys Leu Arg Lys Lys Cys Glu
                165                 170                 175

Lys Glu Glu Lys Lys Met Glu Glu Phe Pro Asp Gln Asp Ile Ser Pro
            180                 185                 190

Leu Pro Gln Pro Ser Ser Arg Asn Lys Ser Arg Lys His Thr Glu Ala
            195                 200                 205

Leu Gln Lys Leu Arg Glu Val Asn Lys Arg Leu Gln Asp Leu Arg Ser
        210                 215                 220

Cys Leu Ser Pro Lys Gln His Gln Ser Pro Ala Leu Gln Ser Thr Asp
225                 230                 235                 240

Asp Glu Val Val Leu Val Glu Gly Pro Val Leu Pro Gln Ser Ser Arg
                245                 250                 255

Leu Phe Thr Leu Lys Ile Arg Cys Arg Ala Asp Leu Val Arg Leu Pro
            260                 265                 270

Val Arg Met Ser Glu Pro Leu Gln Asn Val Val Asp His Met Ala Asn
            275                 280                 285

His Leu Gly Val Ser Pro Asn Arg Ile Leu Leu Leu Phe Gly Glu Ser
        290                 295                 300

Glu Leu Ser Pro Thr Ala Thr Pro Ser Thr Leu Lys Leu Gly Val Ala
305                 310                 315                 320

Asp Ile Ile Asp Cys Val Val Leu Ala Ser Ser Glu Ala Thr Glu
                325                 330                 335

Thr Ser Gln Glu Leu Arg Leu Arg Val Gln Gly Lys Glu Lys His Gln
            340                 345                 350

Met Leu Glu Ile Ser Leu Ser Pro Asp Ser Pro Leu Lys Val Leu Met
            355                 360                 365

Ser His Tyr Glu Glu Ala Met Gly Leu Ser Gly His Lys Leu Ser Phe
        370                 375                 380

Phe Phe Asp Gly Thr Lys Leu Ser Gly Lys Glu Leu Pro Ala Asp Leu
385                 390                 395                 400

Gly Leu Glu Ser Gly Asp Leu Ile Glu Val Trp Gly
                405                 410
```